US012746114B2

(12) United States Patent
Baron et al.

(10) Patent No.: US 12,746,114 B2
(45) Date of Patent: Sep. 29, 2026

(54) NASAL IMPLANTS AND SYSTEMS AND METHOD OF USE

(71) Applicant: Spirox, inc., Maple Grove, MN (US)

(72) Inventors: Scott J. Baron, Menlo Park, CA (US); Michael H. Rosenthal, Menlo Park, CA (US); Brian Domecus, San Francisco, CA (US); Piyush Arora, Fremont, CA (US); Michael Stephan Mirizzi, San Jose, CA (US); Rohit Kulbhushan Girotra, San Francisco, CA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/226,693

(22) Filed: Jul. 26, 2023

(65) Prior Publication Data

US 2023/0363892 A1 Nov. 16, 2023

Related U.S. Application Data

(63) Continuation of application No. 17/215,413, filed on Mar. 29, 2021, now Pat. No. 11,737,865, which is a
(Continued)

(51) Int. Cl.
*A61F 2/18* (2006.01)
*A61B 17/34* (2006.01)
(Continued)

(52) U.S. Cl.
CPC .......... *A61F 2/186* (2013.01); *A61B 17/3468* (2013.01); *A61F 2/18* (2013.01);
(Continued)

(58) Field of Classification Search
CPC .... A61F 2/18; A61F 2/186; A61F 2210/0004; A61F 2310/0097; A61B 17/3468
See application file for complete search history.

(56) References Cited

U.S. PATENT DOCUMENTS 2,173,848 A 9/1939 Kraus
3,395,709 A 8/1968 Rubin
(Continued)

FOREIGN PATENT DOCUMENTS

CN 1279984 10/2006
EP 1216013 B1 6/2006
(Continued)

OTHER PUBLICATIONS

Parylene Engineering (NPL: http://www.paryleneengineering.com/why_use_parylene.htm) accessed Oct. 2, 2017.
(Continued)

*Primary Examiner* — Dinah Baria
(74) *Attorney, Agent, or Firm* — McDonnell Boehnen Hulbert & Berghoff LLP

(57) ABSTRACT

Described are implants for placing in a body, tools for delivering the implants, and systems and methods for using implants and tools for placing in a body and more particularly to nasal implants, tools for delivering nasal implants, and systems and methods for using such implants and tools. A tool may include a hand-held implant delivery device that holds, moves, orients, inserts, or shapes an implant. An implant may be a biodegradable, longitudinal implant that may be oriented for implantation by an implant delivery device.

20 Claims, 32 Drawing Sheets

Related U.S. Application Data continuation of application No. 15/274,986, filed on Sep. 23, 2016, now Pat. No. 10,993,800.

(60) Provisional application No. 62/233,155, filed on Sep. 25, 2015.

(51) Int. Cl.

| | |
|---|---|
| ***A61F 5/56*** | (2006.01) |
| ***A61L 27/50*** | (2006.01) |
| ***A61L 27/54*** | (2006.01) |
| ***A61L 27/58*** | (2006.01) |
| *A61B 17/24* | (2006.01) |

(52) U.S. Cl.

CPC ................ *A61F 5/56* (2013.01); *A61L 27/50* (2013.01); *A61L 27/54* (2013.01); *A61L 27/58* (2013.01); *A61B 2017/248* (2013.01); *A61F 2210/0004* (2013.01); *A61F 2250/0031* (2013.01); *A61F 2310/0097* (2013.01)

(56) References Cited

U.S. PATENT DOCUMENTS

| | | | |
|---|---|---|---|
| 3,716,058 | A | 2/1973 | Tanner, Jr. |
| 4,265,246 | A | 5/1981 | Barry |
| 4,461,281 | A | 7/1984 | Carson |
| 4,645,491 | A | 2/1987 | Evans |
| 4,938,234 | A | 7/1990 | Capriotti |
| 5,131,382 | A | 7/1992 | Meyer |
| 5,163,952 | A | 11/1992 | Froix |
| 5,261,916 | A | 11/1993 | Engelson |
| 5,286,254 | A | 2/1994 | Shapland et al. |
| 5,342,348 | A | 8/1994 | Kaplan |
| 5,356,431 | A | 10/1994 | Pierce |
| 5,358,522 | A | 10/1994 | Montgomery et al. |
| 5,411,550 | A | 5/1995 | Herweck et al. |
| 5,419,760 | A | 5/1995 | Narciso |
| 5,464,450 | A | 11/1995 | Buscemi et al. |
| 5,500,013 | A | 3/1996 | Buscemi et al. |
| 5,531,744 | A | 7/1996 | Nardella et al. |
| 5,533,440 | A | 7/1996 | Sher |
| 5,545,208 | A | 8/1996 | Wolff et al. |
| 5,551,954 | A | 9/1996 | Buscemi et al. |
| 5,591,227 | A | 1/1997 | Dinh et al. |
| 5,637,113 | A | 6/1997 | Tartaglia et al. |
| 5,649,977 | A | 7/1997 | Campbell |
| 5,679,400 | A | 10/1997 | Tuch |
| 5,683,448 | A | 11/1997 | Cragg |
| 5,730,744 | A | 3/1998 | Justin et al. |
| 5,735,811 | A | 4/1998 | Brisken |
| 5,749,893 | A | 5/1998 | Vidal et al. |
| 5,766,237 | A | 6/1998 | Cragg |
| 5,769,883 | A | 6/1998 | Buscemi et al. |
| 5,785,647 | A | 7/1998 | Tompkins et al. |
| 5,837,008 | A | 11/1998 | Berg et al. |
| 5,843,172 | A | 12/1998 | Yan |
| 5,891,108 | A | 4/1999 | Leone et al. |
| 5,893,840 | A | 4/1999 | Hull et al. |
| 5,897,523 | A | 4/1999 | Wright et al. |
| 5,951,586 | A | 9/1999 | Berg et al. |
| 5,972,027 | A | 10/1999 | Johnson |
| 5,980,551 | A | 11/1999 | Summers et al. |
| 5,980,564 | A | 11/1999 | Stinson |
| 5,980,566 | A | 11/1999 | Alt et al. |
| 6,010,054 | A | 1/2000 | Johnson et al. |
| 6,063,101 | A | 5/2000 | Jacobsen et al. |
| 6,071,305 | A | 6/2000 | Brown et al. |
| 6,099,561 | A | 8/2000 | Alt |
| 6,106,541 | A | 8/2000 | Hurbis |
| 6,165,210 | A | 12/2000 | Lau et al. |
| 6,183,433 | B1 | 2/2001 | Bays |
| 6,238,411 | B1 | 5/2001 | Thorner |
| 6,241,747 | B1 | 6/2001 | Ruff |
| 6,241,762 | B1 | 6/2001 | Shanley |
| 6,250,307 | B1 | 6/2001 | Conrad et al. |
| 6,268,405 | B1 | 7/2001 | Yao et al. |
| 6,290,673 | B1 | 9/2001 | Shanley |
| 6,293,967 | B1 | 9/2001 | Shanley |
| 6,322,590 | B1 | 11/2001 | Sillers et al. |
| 6,390,096 | B1 | 5/2002 | Conrad et al. |
| 6,401,717 | B1 | 6/2002 | Conrad et al. |
| 6,415,796 | B1 | 7/2002 | Conrad et al. |
| 6,431,174 | B1 | 8/2002 | Knudson et al. |
| 6,450,169 | B1 | 9/2002 | Conrad et al. |
| 6,454,803 | B1 | 9/2002 | Romo |
| 6,516,806 | B2 | 2/2003 | Knudson et al. |
| 6,656,195 | B2 | 12/2003 | Peters et al. |
| 6,878,165 | B2 | 4/2005 | Makino |
| 6,899,105 | B2 | 5/2005 | Krueger et al. |
| 6,978,781 | B1 | 12/2005 | Jordan |
| 6,982,359 | B1 | 1/2006 | Beaudry |
| 7,055,523 | B1 | 6/2006 | Brown |
| 7,114,495 | B2 | 10/2006 | Lockwood |
| D536,792 | S | 2/2007 | Krueger et al. |
| 7,213,599 | B2 | 5/2007 | Conrad et al. |
| 7,237,554 | B2 | 7/2007 | Conrad et al. |
| 7,322,356 | B2 | 1/2008 | Critzer et al. |
| 7,322,993 | B2 | 1/2008 | Metzger et al. |
| 7,337,781 | B2 | 3/2008 | Vassallo |
| 7,381,222 | B2 | 6/2008 | Pflueger et al. |
| 7,396,232 | B2 | 7/2008 | Fromovich et al. |
| 7,419,497 | B2 | 9/2008 | Muni et al. |
| 7,563,267 | B2 | 7/2009 | Goldfarb et al. |
| 7,666,203 | B2 | 2/2010 | Chanduszko et al. |
| 7,762,940 | B2 | 7/2010 | Henderson et al. |
| 7,780,730 | B2 | 8/2010 | Saidi |
| 7,992,566 | B2 | 8/2011 | Pflueger et al. |
| 8,104,478 | B2 | 1/2012 | Pflueger et al. |
| 8,133,276 | B2 | 3/2012 | Saidi |
| 8,167,787 | B2 | 5/2012 | Gillis |
| 8,267,962 | B2 | 9/2012 | Stupak |
| 8,409,250 | B2 | 4/2013 | Schmieding et al. |
| 8,678,008 | B2 | 3/2014 | Rousseau et al. |
| 8,784,488 | B2 | 7/2014 | Saidi |
| 8,944,990 | B2 | 2/2015 | Hamel et al. |
| 9,480,594 | B2 | 11/2016 | Saidi et al. |
| 2002/0019670 | A1 | 2/2002 | Crawley et al. |
| 2002/0173848 | A1 | 11/2002 | Sachs |
| 2003/0028076 | A1 | 2/2003 | Kuyava et al. |
| 2003/0149447 | A1 | 8/2003 | Morency et al. |
| 2003/0199970 | A1 | 10/2003 | Shanley |
| 2004/0049207 | A1 | 3/2004 | Goldfarb et al. |
| 2004/0098098 | A1 | 5/2004 | McGuckin et al. |
| 2005/0004417 | A1 | 1/2005 | Nelson et al. |
| 2005/0142162 | A1 | 6/2005 | Hunter et al. |
| 2005/0154412 | A1 | 7/2005 | Krueger et al. |
| 2006/0085027 | A1 | 4/2006 | Santin et al. |
| 2006/0147492 | A1 | 7/2006 | Hunter et al. |
| 2006/0184224 | A1 | 8/2006 | Angel |
| 2006/0185680 | A1 | 8/2006 | Bhat et al. |
| 2006/0241650 | A1 | 10/2006 | Weber et al. |
| 2006/0276817 | A1 | 12/2006 | Vassallo et al. |
| 2007/0173848 | A1 | 7/2007 | Lennox et al. |
| 2007/0219575 | A1 | 9/2007 | Mejia |
| 2007/0250118 | A1 | 10/2007 | Masini |
| 2007/0277831 | A1 | 12/2007 | Luhrs |
| 2007/0293946 | A1 | 12/2007 | Gonzales et al. |
| 2008/0021495 | A1 | 1/2008 | Lee et al. |
| 2008/0027480 | A1 | 1/2008 | Van Der Burg et al. |
| 2008/0066794 | A1 | 3/2008 | Durfee |
| 2008/0077240 | A1 | 3/2008 | Saidi |
| 2008/0097335 | A1 | 4/2008 | Trogden et al. |
| 2008/0167628 | A1 | 7/2008 | Li et al. |
| 2008/0208265 | A1 | 8/2008 | Frazier et al. |
| 2008/0234818 | A1 | 9/2008 | Kang et al. |
| 2008/0312688 | A1 | 12/2008 | Nawrocki et al. |
| 2009/0024133 | A1 | 1/2009 | Keady et al. |
| 2009/0024227 | A1 | 1/2009 | Lesh |
| 2009/0099577 | A1 | 4/2009 | Gonzales et al. |
| 2009/0198216 | A1 | 8/2009 | Muni et al. |
| 2009/0204130 | A1 | 8/2009 | Kantsevoy et al. |
| 2009/0274743 | A1 | 11/2009 | Edelman et al. |
| 2009/0312791 | A1 | 12/2009 | Lindh, Sr. et al. |

(56) References Cited

U.S. PATENT DOCUMENTS

| | | | |
|---|---|---|---|
| 2009/0318875 | A1 | 12/2009 | Friedman |
| 2010/0106255 | A1 | 4/2010 | Dubin |
| 2010/0174138 | A1 | 7/2010 | Chang et al. |
| 2010/0280611 | A1 | 11/2010 | Saidi |
| 2011/0004192 | A1 | 1/2011 | Eaton et al. |
| 2011/0009872 | A1 | 1/2011 | Mistry et al. |
| 2011/0251634 | A1 | 10/2011 | Gonzales et al. |
| 2011/0264138 | A1 | 10/2011 | Avelar et al. |
| 2011/0276148 | A1 | 11/2011 | Li et al. |
| 2012/0078367 | A1 | 3/2012 | Hristov et al. |
| 2012/0215307 | A1 | 8/2012 | Chen et al. |
| 2012/0310280 | A1 | 12/2012 | Harrington |
| 2012/0323227 | A1 | 12/2012 | Wolf et al. |
| 2012/0323232 | A1 | 12/2012 | Wolf et al. |
| 2013/0096382 | A1 | 4/2013 | Alexander et al. |
| 2013/0110237 | A1 | 5/2013 | Schaer et al. |
| 2013/0197303 | A1 | 8/2013 | Chun et al. |
| 2013/0217958 | A1 | 8/2013 | Mujwid et al. |
| 2013/0327333 | A1 | 12/2013 | Ng et al. |
| 2014/0000631 | A1 | 1/2014 | Gillis et al. |
| 2014/0188158 | A1 | 7/2014 | Servell et al. |
| 2014/0243975 | A1 | 8/2014 | Saidi et al. |
| 2015/0012090 | A1 | 1/2015 | Saidi |
| 2015/0051449 | A1 | 2/2015 | Qiu |
| 2015/0148902 | A1 | 5/2015 | Komrit |
| 2015/0327806 | A1 | 11/2015 | Kezirian et al. |
| 2016/0058556 | A1 | 3/2016 | Rosenthal et al. |
| 2016/0287367 | A1 | 10/2016 | Rontal |
| 2017/0079774 | A1 | 3/2017 | Saidi et al. |

FOREIGN PATENT DOCUMENTS

| | | | |
|---|---|---|---|
| EP | 1475056 | B1 | 10/2010 |
| EP | 1940320 | B1 | 12/2010 |
| EP | 2692313 | A | 2/2014 |
| EP | 1857078 | A | 3/2016 |
| JP | 2002-523147 | | 7/2002 |
| JP | 2018534097 | A | 11/2018 |
| NO | 2010033682 | A1 | 3/2010 |
| WO | 2000010622 | A1 | 3/2000 |
| WO | 0076493 | A1 | 12/2000 |
| WO | 0101957 | A1 | 1/2001 |
| WO | 0119301 | A1 | 3/2001 |
| WO | 2002076354 | A1 | 10/2002 |
| WO | 2003015664 | A1 | 2/2003 |
| WO | 2003041612 | A2 | 5/2003 |
| WO | 2003/068289 | A1 | 8/2003 |
| WO | 2006093533 | A1 | 9/2006 |
| WO | 2006101610 | A2 | 9/2006 |
| WO | 2006107957 | A2 | 10/2006 |
| WO | 2007134215 | A2 | 11/2007 |
| WO | 2008034031 | | 3/2008 |
| WO | 2008042058 | A1 | 4/2008 |
| WO | 2009036290 | A1 | 3/2009 |
| WO | 2010051273 | A1 | 5/2010 |
| WO | 2010059586 | A1 | 5/2010 |
| WO | 2010132648 | A1 | 11/2010 |
| WO | 2011092161 | A1 | 8/2011 |
| WO | 2012112967 | A1 | 8/2012 |
| WO | 2014004231 | A1 | 1/2014 |
| WO | 2015192162 | A1 | 12/2015 |
| WO | 2016033196 | A1 | 3/2016 |

OTHER PUBLICATIONS

Extended European Search Report issued in European Patent Application No. 16849769.1 dated Apr. 10, 2019.

Barham et al.; Two-dimensional assessment of the nasal valve area cannot predict minimum cross sectional area or airflow resistance; American Journal of Rhinology and Allergy; 30(3); pp. 190-194; May 1, 2016.

Kim et al.; Analysis of cartilage-polydioxanone foil composite grafts; Facial Plast. Surg.; 29(6); pp. 502-505; doi:10.1055/s-0033-1360593; (Author Manuscript); Dec. 2013.

De Pochat et al.; The role of septa I cartilage in rhinoplasty: Cadaveric analysis and assessment of graft selection; Aesthetic Surgery Journal; 31 (8); pp. 891-896; Nov. 2011.

Friedman et al.; A simplified technique for airway correction at the nasal valve area; Otolaryngol Head Neck Surg; 131 (4); pp. 519-524; Oct. 2004.

Kalan et al.; Treatment of external nasal valve (alar rim) collapse with an alar strut; Journal of Laryngology and Otology; 115(10); pp. 788-791; Oct. 2001.

Karen et al.; The use of percutaneous sutures for graft fixation in rhinoplasty; Archives Facial Plastic Surgery; 5(2); pp. 193-196; Mar.-Apr. 2003.

Lambert et al.; A new method for arterial drug delivery via removable stent (abstract); JACC; 21 (2); p. 483A; Abstract No. 834-2; Feb. 1993.

Millman; Alar Batten grafting for management of collapsed nasal valve; Laryngoscope; 112(3); pp. 574-579; Mar. 2002.

Pochat et al.; The role of septa! cartilage in rhinoplasty: cadaveric analysis and assessment of graft selection; Aesthetic Surgery Journal; 31(8); pp. 891-896; Nov. 2011.

Rhee et al.; Nasal valve surgery improves disease-specific quality of life; Laryngoscope; 115(3); pp. 437-440; Mar. 2005.

Westreich et al.; Defining nasal cartilage elasticity: Biomechanical testing of the tripod theory based on a cantilevered model; Arch Facial Plast Surg; 9(4); pp. 264-270; Jul./Aug. 2007.

Cole; Biophysics of nasal air flow: A review; American Journal of Rhinology; 14(4); pp. 245-249; Jul./Aug. 2000.

Cole; The four components of the nasal valve; American Journal of Rhinology; 17(2); pp. 107-110; Mar./Apr. 2003.

Fanous et al.; Collapsed nasal-valve widening by composite grafting to the nasal floor; Journal of Otolaryngology; 25(5); pp. 313-316; Oct. 1996.

Friedman et al.; Nasal Valve Suspension: An Improved, Simplified Technique for Nasal Valve Collapse; Laryngoscope; 113(2); pp. 381-385; Jan. 2003.

Gonzales et al.; U.S. Appl. No. 15/423,345 entitled "Apparatus and methods for correcting nasal valve collapse," filed Feb. 2, 2017.

DETAIL A

DETAIL B

SECTION C-C

NASAL IMPLANTS AND SYSTEMS AND METHOD OF USE

CROSS REFERENCE TO RELATED APPLICATIONS

This application is a continuation of U.S. patent application Ser. No. 17/215,413, filed Mar. 29, 2021, which is a continuation of U.S. patent application Ser. No. 15/274,986, filed Sep. 23, 2016, which claims priority to U.S. Provisional Patent Application No. 62/233,155, filed Sep. 25, 2015 titled "Nasal Implants and Systems and Method of Use", the disclosures of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention pertains to implants for placing in a body, tools for delivering the implants, and systems and methods for using implants and tools for placing in a body and more particularly to nasal implants, tools for delivering nasal implants, and systems and methods for using such implants and tools.

BACKGROUND

The particular nasal anatomy of an individual may cause or contribute to various problems, such as cosmetic concerns, difficulty breathing, sleep apnea, or snoring, and impact an individual's health or reduce the quality of life. For example, the structure of an external or internal nasal valve may resist airflow from the nose to the lungs and prevent an individual from getting sufficient oxygen to the blood.

U.S. Pat. Nos. 8,133,276, 7,780,730, and U.S. 2012/0109298 describe implants that can be introduced into the nasal region of an individual using non-surgical injection techniques for treating a nasal valve of an individual.

There is a continued need for improvements to address problems attributed to nasal anatomy that are easier to use, last longer, are less invasive, are less expensive to manufacture, work better and so on.

SUMMARY OF THE DISCLOSURE

Described herein are implants for placing in a body, tools for delivering the implants, and systems and methods for using implants and tools for placing in a body and more particularly to nasal implants, tools for delivering nasal implants, and systems and methods for using such implants and tools.

In general, in one embodiment, a nasal implant delivery tool including a handle including an implant loading chamber adapted to receive a nasal implant; a needle extending distally from the handle, the needle having a lumen with a portion of the lumen having a non-circular cross-section, the needle having a sharp distal end; and an actuator adapted to move the nasal implant along the needle lumen and out of an opening at the distal end of the needle This and other embodiments can include one or more of the following features. The delivery tool actuator can further include a push-rod and plunger assembly. The delivery tool can further include a compression element coupling the push-rod to the plunger assembly. The delivery tool can further include a push rod locking element proximal to the implant loading chamber configured to prevent further proximal movement of the push rod relative to the handle. The needle can be movable relative to the handle between a plurality of discrete positions, the plurality of discrete positions can correspond to a length of the nasal implant. The delivery tool can further include a needle slider actuator configured to move the needle between a plurality of discrete positions relative to the handle. A length of the actuator can be adjustable between a first position and a second position. The actuator can include a push-rod and plunger assembly and a length of the push-rod and plunger assembly can be adjustable between a first position and a second position by engaging the push-rod with a first locking surface on the plunger assembly and a second locking surface on the plunger assembly. The delivery tool can further include an implant orientation indicator configured to provide a visual indication of a plane formed by a first arm and a second arm of the nasal implant in the deployed configuration corresponding to the orientation of the implant within the needle lumen. The implant orientation indicator can include a first arm projecting from the handle in a first direction and a second arm projecting from the handle in a second direction. The first arm and second arm can define a plane that can be substantially similar to the plane formed by the first arm and the second arm of the nasal implant in the deployed configuration corresponding to the orientation of the implant within the needle lumen. The implant loading chamber can be in communication with the needle lumen and can be adapted to load the nasal implant into the needle lumen. The implant loading chamber can be adapted to move the nasal implant from a deployed configuration to a delivery configuration as the nasal implant is advanced into the needle lumen. The implant loading chamber can be in communication with an implant engagement surface disposed between the needle lumen and implant loading chamber. The implant engagement surface can be adapted to engage with a first arm and a second arm of the implant to move the implant between a deployed configuration and a delivery configuration. The implant engagement surface can include a substantially smooth inner surface. The implant loading chamber can be configured to receive any of the nasal implants in a deployed configuration. The implant loading chamber can include a first recess and a second recess adapted to provide a passage for a tweezer engaged with the nasal implant in the deployed configuration. The implant loading chamber can be adapted to receive a cartridge containing the nasal implant. The cartridge can be configured to contain two or more nasal implants. The delivery tool cartridge can further include an implant engagement ramp adapted to engage with a first arm and a second arm of the implant to move the implant between a deployed configuration and a delivery configuration. The cartridge can be adapted to be in communication with the needle lumen. The handle can be adapted to receive the cartridge such that the cartridge engages with the needle lumen to adjust a length of the needle lumen relative to the handle. The needle can include a low friction coating on an external surface of the needle. The low friction coating can be selected from the group consisting of: PTFE, silicone, and poly(p-xylylene). The delivery tool can further include an actuator register adapted to indicate a position of the actuator at which the nasal implant can be at the distal end of the needle lumen. The actuator register can include a marking on the actuator or on the handle. The delivery tool can further include an actuator register adapted to indicate a position of the actuator at which at least a distal portion of the implant can be moved out of the needle lumen. The actuator register can be a stop element preventing further movement of the actuator. The needle can include substantially banded markings at various positions along the needle. The delivery tool can further include any of the described nasal implants. The delivery tool can further include a cartridge containing the nasal implant. The delivery tool can further include a cartridge containing two or more nasal implants. A system can include any of the described delivery tools or nasal implants.

In general, in one embodiment, a nasal implant including a body including a distal end; a proximal end; a central portion disposed between the proximal end and the distal end; a first arm disposed at the distal end, the arm having a proximal end fixed to the body and a distal end not fixed to the body, the distal end of the arm being adapted to move away from a central longitudinal axis of the body from a delivery configuration toward a deployed configuration; and a second arm having a proximal end fixed to the body and a distal end not fixed to the body, the distal end of the second arm being adapted to move away from a central longitudinal axis of the body from a delivery configuration toward a deployed configuration.

This and other embodiments can include one or more of the following features. The first and second arms can be biased toward their deployed configuration. The first and second arms can be configured to self-expand toward the deployed configuration. The central portion can include a plurality of small projections. The implant can further include a blunt proximal end. The implant can further include a plurality of barbs at the proximal end. The implant can include an inner degradable portion and an outer coating including a hydrophobic material. The hydrophobic material can be poly(caprolactone). The hydrophobic material can be Parylene™ The hydrophobic material can be a bioabsorbable material. The hydrophobic material can be not a bioabsorbable material. The hydrophobic material can cover an entire outer surface of the inner degradable portion. The hydrophobic material can cover a portion of an outer surface of the inner degradable portion. The portion of the outer surface can include the central portion of the implant. The portion of the outer surface can include the central portion and the distal end of the implant. The hydrophobic material can have a discontinuous pattern over the outer surface of the inner degradable portion. The hydrophobic material can have a thickness of about 0.1 micron to about 10 microns. The hydrophobic material can have a thickness of about 0.1 micron to about 5 microns. The hydrophobic material can have a thickness of about 0.1 micron to about 1 micron. The hydrophobic material can have a thickness of less than about 10 microns. The hydrophobic material can have a thickness of less than about 5 microns. The hydrophobic material can have a thickness of less than about 1 micron. The outer coating can include the hydrophobic material having a thickness selected to achieve a pre-determined degradation profile. The implant can further include an agent in the hydrophobic material or disposed between the inner degradable portion and the outer coating including the hydrophobic material. The agent can be selected from the group consisting of: an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a radiopaque agent, radiolabeled agent, a steroid, and a vitamin. The agent can be a bioactive agent and the hydrophobic material can be configured to elute one or more bioactive agents selected from the group consisting of: thrombolytics, corticosteroids, vasodilators, antihypertensive agents, antimicrobials or antibiotics, antimitotics, antiproliferatives, antisecretory agents, non-steroidal anti-inflammatory drugs, immunosuppressive agents, growth factors, growth factor antagonists, antitumor and/or chemotherapeutic agents, antipolymerases, antiviral agents, photodynamic therapy agents, antibody targeted therapy agents, prodrugs, free radical scavengers, antioxidants, biologic agents, and radiotherapeutic agents. The central portion can have a flexural rigidity of about 9-130 N-mm$^2$.

In general, in one embodiment, a method of supporting a tissue section of a patient's nose, the method including inserting a needle of a delivery tool into tissue of the nose, the delivery tool including a handle portion with the needle extending distally from the handle, the needle including a needle lumen, the handle including an implant loading chamber adapted to receive an implant, the delivery tool including an actuator adapted to move the implant along the needle lumen and out of an opening at the distal end of the needle; advancing the implant distally from the needle lumen to place a distal end of the implant within the nasal tissue, the implant including a first arm at a distal end of the implant and a second arm at the distal end of the implant; the first arm moving away from a central longitudinal axis of the implant during the advancing step, the second arm moving away from the central longitudinal axis of the implant during the advancing step; withdrawing the delivery tool to dispose a central portion of the implant within the nasal tissue; and supporting the tissue section with the implant.

This and other embodiments can include one or more of the following features. Advancing the implant can include pushing the implant distally such that the first arm and second arm each can engage the tissue thereby moving away from the central longitudinal axis of the implant. The actuator can include a push-rod and plunger assembly with a compression element coupling the push-rod to the plunger assembly, advancing the implant can include pushing the implant distally with the push-rod. The method can further include continuing to provide a distal axial force on the implant with the push-rod and compression element while initially withdrawing the delivery tool. The method can further include loading the implant into the implant loading chamber of the delivery tool. The method can further include loading the implant into the implant loading chamber using tweezers. The method can further include loading a cartridge containing the implant into the implant loading chamber. The method can further include retracting a push-rod of the actuator to a proximal locking point prior to loading the implant in the implant loading chamber. The method can further include adjusting a length of the needle extending from the handle prior to loading the implant. Sliding the needle relative to the handle can include moving a slider on the handle coupled to the needle to move the needle between a plurality of discrete positions relative to the handle. The actuator can include a push-rod and plunger assembly, can further include adjusting a length of the push-rod and plunger assembly prior to loading the implant. The method can further include advancing the implant from the implant loading chamber into the needle lumen. The delivery tool can include an implant engagement surface disposed between the needle lumen and implant loading chamber, can further include advancing the implant from the implant loading chamber through the implant engagement surface and into the needle lumen. The loading step can include loading the implant into a proximal end of the needle and advancing the implant to the distal end of the needle prior to the inserting step. The loading step can include collapsing the first arm and second arm of the implant prior to entering the proximal end of the needle. Advancing the implant can include advancing the actuator to a locking point followed by unlocking the actuator prior to advancing the implant distally from the needle lumen to place the distal end of the implant within the nasal tissue. The inserting step can include inserting a distal end of the needle into tissue of the nose. The method can further include maintaining a known orientation between the implant and the needle during the inserting step. Maintaining the known orientation between the implant and the needle can include engaging the implant with a portion of a lumen of the needle having a non-circular cross section. The implant can include an inner degradable portion and an outer coating including a hydrophobic material. The hydrophobic material can be poly(caprolactone). The hydrophobic material can be Parylene™. The hydrophobic material can be a bioabsorbable material. The hydrophobic material can be not a bioabsorbable material. The hydrophobic material can cover an entire outer surface of the inner degradable portion. The hydrophobic material can cover a portion of an outer surface of the inner degradable portion. The portion of the outer surface can include the central portion of the implant. The portion of the outer surface can include the central portion and the distal end of the implant. The hydrophobic material can have a discontinuous pattern over the outer surface of the inner degradable portion. The hydrophobic material can have a thickness of about 0.1 micron to about 10 microns. The hydrophobic material can have a thickness of about 0.1 micron to about 5 microns. The hydrophobic material can have a thickness of about 0.1 micron to about 1 micron. The hydrophobic material can have a thickness of less than about 10 microns. The hydrophobic material can have a thickness of less than about 5 microns. The hydrophobic material can have a thickness of less than about 1 micron. The method can further include selecting the implant based on a degradation profile of the implant. The degradation profile of the implant can be based on the inner degradable portion and the outer coating including the hydrophobic material. The method can further include selecting a conformality and thickness of the outer coating based on a desired degradation profile of the implant. The method can further include degrading the inner degradable portion of the implant. Degrading the inner degradable portion of the implant can take less than about 48 months. Degrading the inner degradable portion of the implant can take less than about 36 months. Degrading the inner degradable portion of the implant can take less than about 24 months. Degrading the inner degradable portion of the implant can take less than about 18 months. Degrading the inner degradable portion of the implant can take less than about 12 months. Degrading the inner degradable portion of the implant can take less than about 9 months. Degrading the inner degradable portion of the implant can take less than about 6 months. Degrading the inner degradable portion of the implant can take less than about 3 months. Degrading the inner degradable portion of the implant can take less than about 1 month. The method can further include the implant eluting an agent into the nasal tissue. The agent can be selected from the group consisting of: an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a radiopaque agent, radiolabeled agent, a steroid, and a vitamin. The agent can be a bioactive agent and the hydrophobic material is configured to elute one or more bioactive agents selected from the group consisting of: thrombolytics, corticosteroids, vasodilators, antihypertensive agents, antimicrobials or antibiotics, antimitotics, antiproliferatives, antisecretory agents, non-steroidal anti-inflammatory drugs, immunosuppressive agents, growth factors, growth factor antagonists, antitumor and/or chemotherapeutic agents, antipolymerases, antiviral agents, photodynamic therapy agents, antibody targeted therapy agents, prodrugs, free radical scavengers, antioxidants, biologic agents, and radiotherapeutic agents. The implant can include the agent in a hydrophobic material of the implant or disposed between an inner degradable portion and an outer coating including the hydrophobic material of the implant. The delivery tool can be any of the previously described delivery tools. The implant can be any of the previously described nasal implants.

In general, in one embodiment, a method for making a nasal implant including providing a biodegradable inner portion of the nasal implant; selecting a desired biodegradation profile; and applying a hydrophobic material with a pre-selected pattern and thickness that corresponds to the desired biodegradation profile for the biodegradable inner portion of the nasal implant.

This and other embodiments can include one or more of the following features. The hydrophobic material can be poly(caprolactone). The hydrophobic material can be Parylene™ The hydrophobic material can be a bioabsorbable material. The hydrophobic material can be not a bioabsorbable material. The hydrophobic material can cover an entire outer surface of the inner degradable portion. The hydrophobic material can cover a portion of an outer surface of the inner degradable portion. The portion of the outer surface can include a central portion of the implant. The portion of the outer surface can include a central portion and a distal end of the implant. The hydrophobic material can have a discontinuous pattern over the outer surface of the inner degradable portion. The hydrophobic material can have a thickness of about 0.1 micron to about 10 microns. The hydrophobic material can have a thickness of about 0.1 micron to about 5 microns. The hydrophobic material can have a thickness of about 0.1 micron to about 1 micron. The hydrophobic material can have a thickness of less than about 10 microns. The hydrophobic material can have a thickness of less than about 5 microns. The hydrophobic material can have a thickness of less than about 1 micron. The desired biodegradation profile can include a time period of less than about 48 months. The desired biodegradation profile can include a time period of less than about 36 months. The desired biodegradation profile can include a time period of less than about 24 months. The desired biodegradation profile can include a time period of less than about 18 months. The desired biodegradation profile can include a time period of less than about 12 months. The desired biodegradation profile can include a time period of less than about 9 months. The desired biodegradation profile can include a time period of less than about 6 months. The desired biodegradation profile can include a time period of less than about 3 months. The desired biodegradation profile can include a time period of less than about 1 month.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
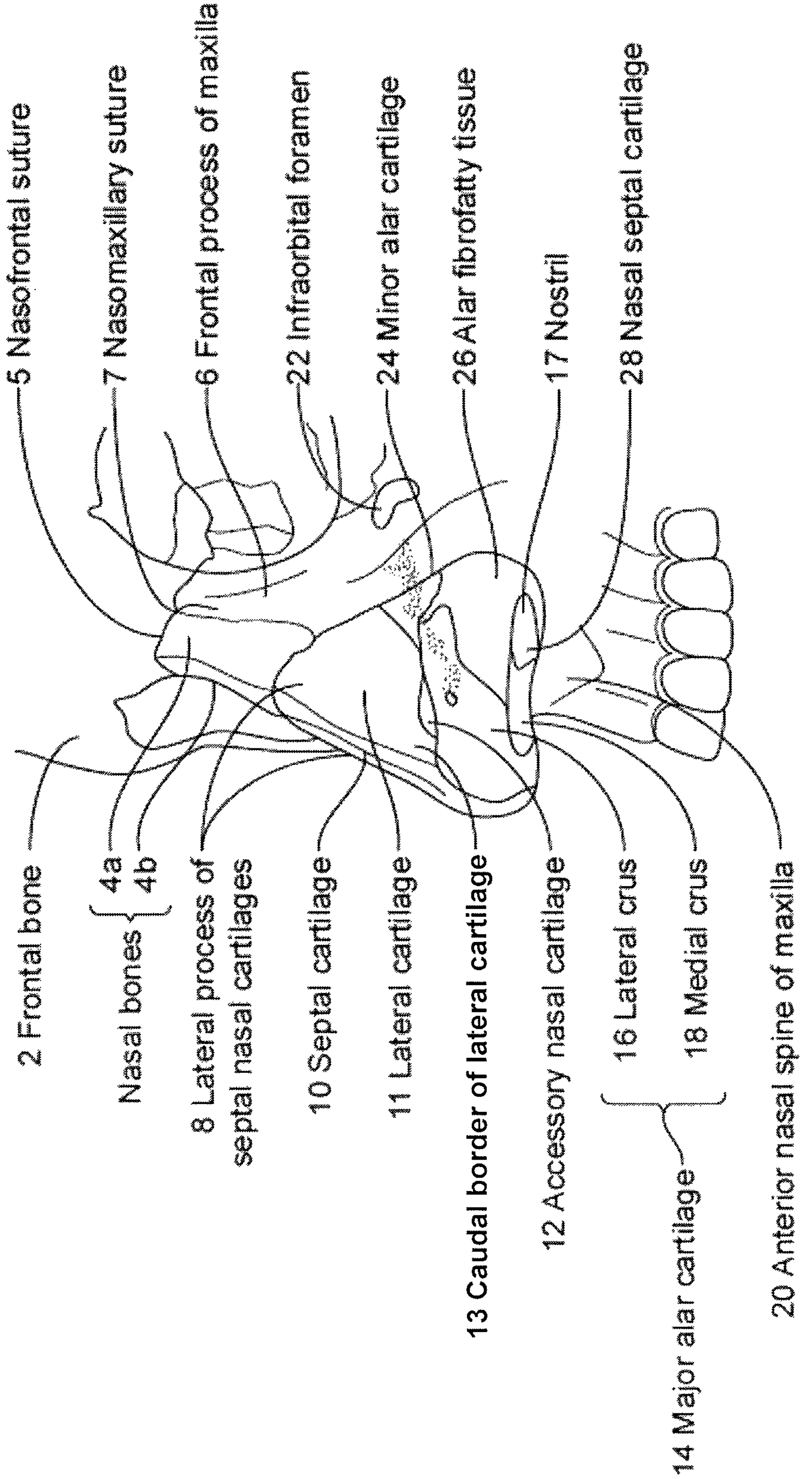
FIG. 1 shows the underlying structural anatomy and tissues of a nose on a face without overlying skin or tissue.

Described herein are implants, devices, systems and methods using implants, devices and systems for altering, enhancing, repairing, and supporting a body tissue. Such systems and methods may be used to support or change any tissue in the body, but may be especially beneficial for use in nasal tissue in a patient's nose, such as to aid breathing or change the cosmetic appearance of the nose. A system as described herein generally includes an implant to be placed into a patient's body, an implant delivery tool to deliver the implant to the patient and an actuator adapted to move the nasal implant through the delivery tool, although the system components may instead be used separately from one another. An implant delivery tool may include a handle and a piercing end (a needle) for piercing a body tissue. An implant may be sufficiently strong to provide support to a tissue or to change a tissue shape when the implant is in place in the body. An implant may also be sufficiently flexible to change shape during implant delivery or allow tissue to move when the implant is in place in the body. An implant delivery tool may be a handheld delivery tool and may be configured to place an implant relatively close to the surface of the body, such as under or in cartilage or other connective tissue, muscle or skin. An implant delivery tool may have a small piercing end (needle) for making a small, relatively unobtrusive opening through a surface of the body (such as through skin, mucous, or epithelium) and moving through underlying tissues to deliver an implant to the patient. An implant delivery tool may deliver the implant to the tissue through the opening in the body in a minimally invasive way and may cause only minimal scarring. In addition to minimizing pain, infection, and swelling, such a minimally invasive system and methods described herein may also make unnecessary the use of large bandages to cover the opening in the skin and tissues after implant delivery which can otherwise cause patient discomfort or bring unwanted attention. This may especially be important if the patient receives an implant in a highly visible location, such as receiving a nasal implant in a nose and the bandage is on the person's face. In some cases implant delivery may be very fast, taking only seconds or minutes to perform. A system and method as described herein may be very safe and generally does not require a surgical procedure. In addition to being performed in a hospital, it can generally also be performed in a doctor's office or outpatient facility or another care facility outside a hospital. A delivery tool for delivering an implant into a patient's body may make a small hole that easily heals by using a relatively small needle (similar in size to a needle used for drawing blood or placing an IV (intravenous) line into a patient) for placing the implant in the body.

An implant may be placed near the skin's surface or may be placed deeply into a body tissue. An implant may be shaped to have a low profile in at least one dimension (e.g., height) so that it can lie relatively flatly against tissue when implanted. In the case of a nasal implant placed near the surface of a patient's nose, an implant may have such a low profile that the presence of the implant is not obvious from looking at the patient.

An implant may be able to take on different configurations or different shapes, such as having a delivery configuration during implant delivery, a deployment configuration when fully deployed, and other configurations before, during, or after delivery or deployment. An implant may have a contracted configuration and an expanded configuration. An implant may be contracted or configured to contract to fit in an implant delivery tool and fit through a small placement hole made by the delivery tool. An implant may be configured to expand in a body tissue when placed in a patient to carry out its supporting or tissue shaping function. An expanded implant may better support or alter a body structure or tissue or may help hold an implant in place. An implant may have an implant body and a projection, and the projection may be able to move independently or relative to the implant body. A projection may move from an outward position towards the central longitudinal axis of the implant, contracting the overall profile of the implant so that an implant with a relatively larger cross-sectional profile can fit (temporarily) into a relatively smaller region of a delivery device before the implant takes on an expanded configuration in the body tissue. An end may be forked and two or more implant projections (e.g., arms on the end of the fork) may also move towards each other and together contract the overall implant profile or may diverge (e.g., move away from each other) and expand the overall implant profile. An implant may include an elastomeric or other flexible material so that the implant body or projections (arms) can change shape without breaking. An implant or a portion of an implant such as an arm may have a curvilinear or arc shape over part or all of the implant or implant portion. An implant, especially an implant projection (arm) may include one or more features, such as bevels, that may be useful for guiding the implant into an implant delivery tool or for guiding the implant into a tissue. A bevel may be on an end of a projection.

Implants, devices, systems and methods as described herein may be used in any body tissue, but may be especially useful for supporting or altering a nasal internal valve or other nasal tissue. The internal nasal valve is a complex 3-dimensional structure that controls respiration and how air (oxygen) enters into and exits from the body. Dysfunction in the internal nasal valve has a dramatic and negative effect on a person's ability to breathe.

FIG. 1 shows the underlying structural anatomy and tissues of a face. The outer layers of overlying skin and muscle have been removed to better show the underlying cartilage and bone that provide structure. The nose sits in the middle of the face and has important responsibilities in olfaction (smelling) and controlling respiration. The nose controls respiration by restricting the flow of air. The nose has two airflow pathways, one on each side of the nose (starting with each nostril) which combine to form a single airflow pathway into the body. Air from the nose flows through the trachea and into the lungs where the air is spread out in the lobules of the lungs and oxygen is absorbed for use by the entire body. Each of the two airflow pathways in the nose have several segments including two types of nasal valves (called external nasal valves and internal nasal valves) along each nasal airflow pathway that act to control airflow through the nose and so together the external and internal valves control airflow into and out of the body. The amount of airflow resistance caused by the valves needs to be "just right"; either too much or too little resistance causes breathing and other problems. The valves are tissues that surround the airflow and the amount of resistance they provide to the airflow is determined largely by their shape and their size (their internal cross-sectional area). The internal nasal valve on each pathway is the narrowest segment of the pathway in the nose and generally creates most of the resistance. Besides the important function of controlling airflow, the internal nasal valves also help give the nose its distinctive shape. A nasal valve is shaped and supported by various structures in the nose and face, with upper lateral cartilage playing a significant role in its form and function. Large and even small changes in internal nasal valve structure can impair nasal breathing, as well as change the cosmetic appearance of the nose. These changes generally act to reduce the cross-sectional area of the internal valve, and can be caused by surgery, another medical treatment, or trauma to the face. Additionally, there are variations of nasal valve structure between individuals, with some individuals having significantly narrowed valves due to weakened or misshaped cartilage, commonly observed as a pinched nose. A narrowed valve region increases the acceleration of airflow and simultaneously decreases intraluminal pressure, causing the valves to collapse. While even normal nasal valves can collapse under great respiratory pressures, dysfunctional internal valves can collapse even during normal breathing, with reduced oxygen flow, snoring and mouth breathing as undesirable consequences.

The nose includes the external nose that protrudes from the face and a nasal cavity underneath the external nose. From top to bottom, the external nose has a root, a bridge, a dorsum (ridge), a free tip (apex), and a columella. The external nose is appended to the piriform aperture, the continuous free edges of the pear shaped opening of the nasal cavity in the skull and is formed by the nasal bones and the maxilla. As shown in FIG. 1, the nose sits in the middle of the face, framed by the bones of the head, with frontal bone 2 superior to the nose, lateral maxilla frontal process 6 lateral to it, and the maxilla anterior nasal spine 20 inferior to it. (Another lateral maxilla frontal process on the other side of the nose is not visible in this view). The external nose can be roughly divided into three layers from outside to inside: an overlying skin and muscle layer (removed in this view), a middle cartilage and bony framework layer, and an inner mucosal layer (not readily visible in this view).

While the middle cartilage and bony framework layer provides form, structure, and support to the nose, it is also organized to allow the nose to be flexible and wiggle and bend in different directions. It can also be roughly divided into three sections: from top to bottom, they are an upper (superior) bony third, and middle and lower (inferior) cartilaginous thirds. The upper third includes paired left nasal bone **4*a* and right nasal bone 4*b* that are joined in the middle of the nose and form the top (or superior) part of the bridge of the nose. Nasal bone 4*a* (along with lateral maxilla frontal process 6) joins frontal bone 2 superiorly to form the nasofrontal (nasion) suture line 5. Laterally, nasal bone 4*a* joins the maxilla at its frontal process 6 to form a fibrous joint at the maxilla nasal bone suture line 7 (or nasomaxillary suture line). The middle third of the cartilage and bony framework layer includes septal cartilage 10 which forms part of the septum of the nose and internally separates the nostrils and the two airflow pathways. Lateral process 8 of septal cartilage 10 merges superiorly with upper lateral cartilage 11. (Another lateral process on the other side of the nose that merges with upper lateral cartilage on the other side of the nose is not visible in this view). FIG. 1 also shows minor alar cartilage 24, one of several accessory cartilages which provide support and allow movement of the nose, and which impact the complex 3-dimensional shape of the nose. Upper lateral cartilage 11 is normally fairly stiff and it has much of the responsibility for supporting the side of the nose. In conjunction with septal cartilage tissue, it helps to form the internal nasal valve, which is inside the nose under the upper lateral cartilage and not readily visible in this view. As mentioned above, there are two internal nasal valves (one on either side of the nose). Each internal nasal valve is formed by and bordered medially by septal cartilage 10, laterally by the caudal margin 13** of the upper lateral cartilage, and inferiorly by the head of inferior turbinate (not visible in this view) and surrounds an opening through which air flows. The attachment of the upper lateral cartilage to the septum (septal cartilage) forms an angle that defines the internal nasal valve angle (also called simply "valve angle"). The internal nasal valve angle is the narrowest part of the nasal airway and creates resistance that controls airflow through it. There is some natural variation between individuals in their nasal valve angles, and valve angles may change over time as a natural consequence of aging. Valve angle is determined in part by genetics, and an ethnic group has a particular average valve angle associated with it. There is also variation in valve angles between individuals, even within a particular ethnic group, and between an individual's left and right valves. Nasal valve angles may also be altered as a result of surgery, trauma or another intervention. A valve with a valve angle of less than about 10 degrees may generally be considered collapsed, causing nasal airway obstruction with nasal sidewall collapse upon inspiration and may merit treatment such as described herein. A valve angle that is greater 10 degrees may also cause some airway obstruction, cosmetic concern or another concern and may also merit treatment but its dysfunction is generally not as severe as a collapsed valve. Valves in need of treatment may be candidates for treatment using the implants, devices, systems and methods described herein.

The lower third of the cartilage and bony framework layer includes major alar cartilage (also referred to as lower lateral cartilage or inferior lateral cartilage, based on its location and to distinguish it from upper lateral cartilage) that help shape the nostrils and the tip of the nose. This cartilage is softer and more mobile than upper lateral cartilage, and it allows the tip of the nose to move. Major alar cartilage 14 is U shaped and includes lateral crus 16 and medial crus 18. Major alar cartilage 14 forms part of external valve around nostril 17 (also called nares), though it does not quite reach the bone laterally. The lower third of the cartilage and bony framework layer also includes alar fibrofatty tissue 26 of alar that fills the gap between lateral crus 16 and the bone. FIG. 1 also shows small accessory alar cartilage 12 that links the major alar and lateral cartilage 8 of the cartilage and bony framework layer.

Figure 2A:
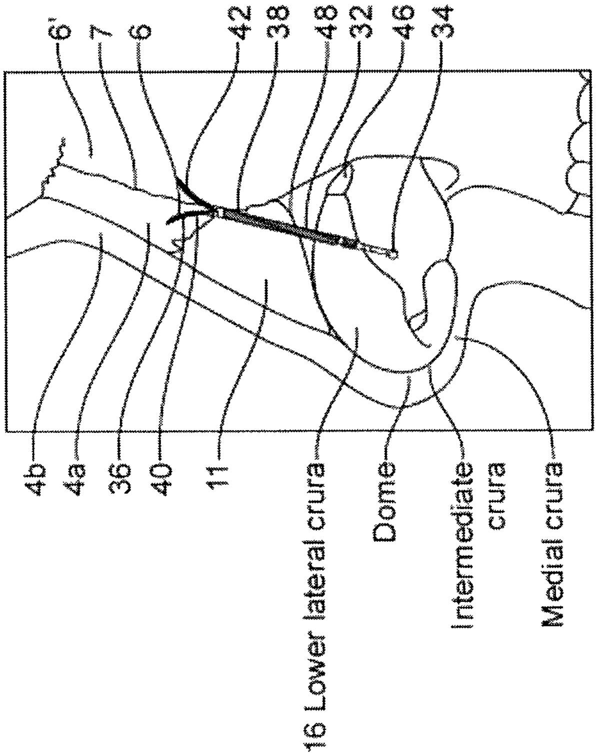
FIGS. 2A-2B show placement of an implant in a patient's nose.
Figure 2B:
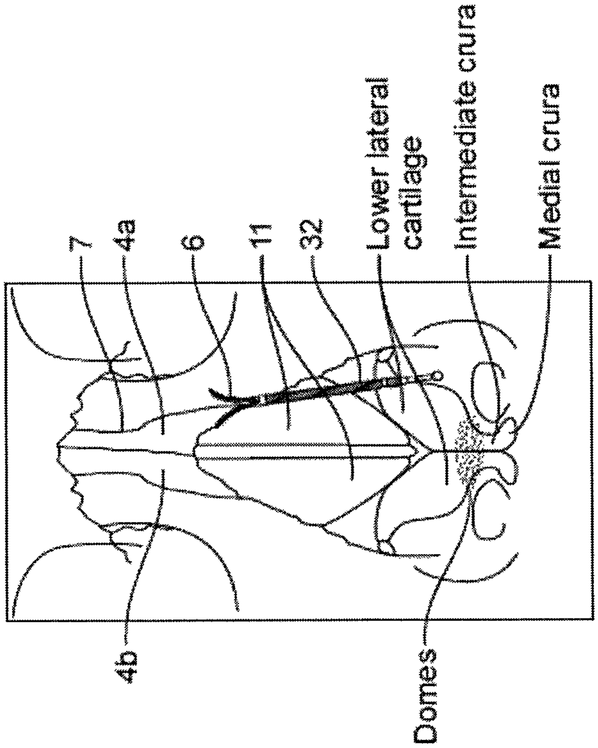

As mentioned above, the nose is a complex, 3-dimensional structure. It may be desirable to change its shape or better support its structure in order to improve or maintain its function or appearance (cosmesis), but it can difficult to change one aspect of the nose without adversely affecting another part. Indeed, previous surgical interventions are one cause of altered nasal valve function that may be treated using the systems and methods described herein. Described herein are implants, devices, systems and methods function for changing or supporting an aspect of a body structure or shape, including of the nose. FIGS. 2A-2B show front and side views, respectively, of an implant 32 implanted in a patient's nose and supporting a tissue section of a patient's nose. Implant 32 may be useful for maintaining or improving nasal function or appearance. Implant 32 is underlying the skin and muscles which have been removed to better illustrate the implant and the underlying nasal structures and implant. FIGS. 2A-2B show implant 32 in place for supporting or changing an internal nasal valve. Implant 32 apposes structures in the cartilage and bony framework layer under the skin and muscle. Implant 32 has a body with proximal end 34, distal end 36 and central portion 38 between the proximal and distal ends. Central portion 38 is in a position between the nasal cartilage and patient skin or muscle. Central portion 38 apposes upper lateral cartilage 11 and lower lateral crus 16 of the lower lateral cartilage. As mentioned above, along with the septal cartilage, the caudal end of the upper lateral cartilage defines the internal valve angle, and central portion 38 of implant 32 also apposes the caudal end 48 of the upper lateral cartilage 11 and so overlies or acts on the internal valve wall, providing support to or changing a shape of the internal valve. Distal end 36 of implant 32 apposes structures in the upper part of cartilage and bony framework. In these examples in FIGS. 2A-2B, distal end 36 of implant 32 is forked with first arm 40 and second arm 42 forming the tines of the fork. Each arm has a proximal end fixed to the implant body and a distal end not fixed to the body. In this example, the arms apposes nasal bone 4*a*, frontal process 6 of the maxilla bone, and maxilla nasal bone suture line 7 (nasomaxillary suture line). In some variations, a distal end of an implant may be apposed or in proximity to one of more structures in the upper layer or any of the structures or tissues in the middle or lower cartilage and bony framework layer (e.g., accessory cartilage, major alar cartilage, minor alar cartilage, septal cartilage, maxilla, etc.).

Delivery tools are disclosed herein to deliver the implant configurations disclosed herein to a target location within a patient's body. Examples of delivery tools include nasal implant delivery tools.

Additional examples of nasal implants and delivery tools are disclosed in U.S. Patent Application No. 62/042,209 filed Aug. 26, 2014 and U.S. patent application Ser. No. 14/836,841 filed Aug. 2, 2015, the disclosures of each which are incorporated herein by reference in their entirety. Any of the nasal implants disclosed in U.S. Patent Application No. 62/042,209 and U.S. patent application Ser. No. 14/836,841 can be used with the delivery tools disclosed herein.

The delivery tools can include a handle including an implant loading chamber adapted to receive a nasal implant, a needle extending distally from the handle, the needle having a lumen with a portion of the lumen having a non-circular cross-section, the needle having a sharp distal end, and an actuator adapted to move the nasal implant along the needle lumen and out of an opening at the distal end of the needle.

Figure 5:
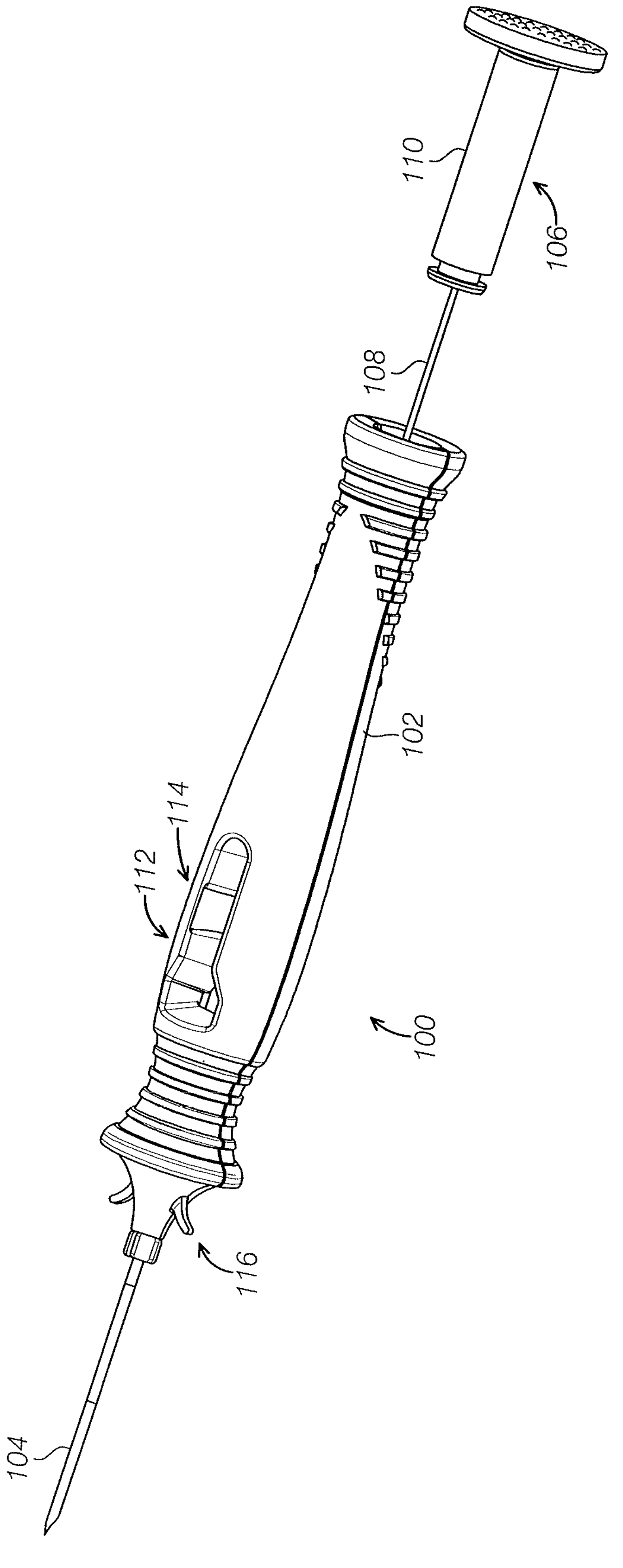
FIG. 5 shows an implant delivery device for placing an implant into a body tissue.

FIG. 5 shows an implant delivery device 100 for placing an implant into a body tissue. The delivery tool 100 includes a handle 102, needle 104 with a needle lumen, and an actuator 106 including a push rod 108 and plunger assembly 110. The handle 102 includes an implant loading chamber 112 adapted to receive the nasal implant.

The implant loading chamber 112 includes recesses 114 that can be adapted to allow for tweezers to be used to place the implant in the implant loading chamber 112. The recesses 114 can include a first recess and a second recess adapted to provide a passage for a tweezer engaged with the nasal implant in the deployed configuration.

Figure 6:
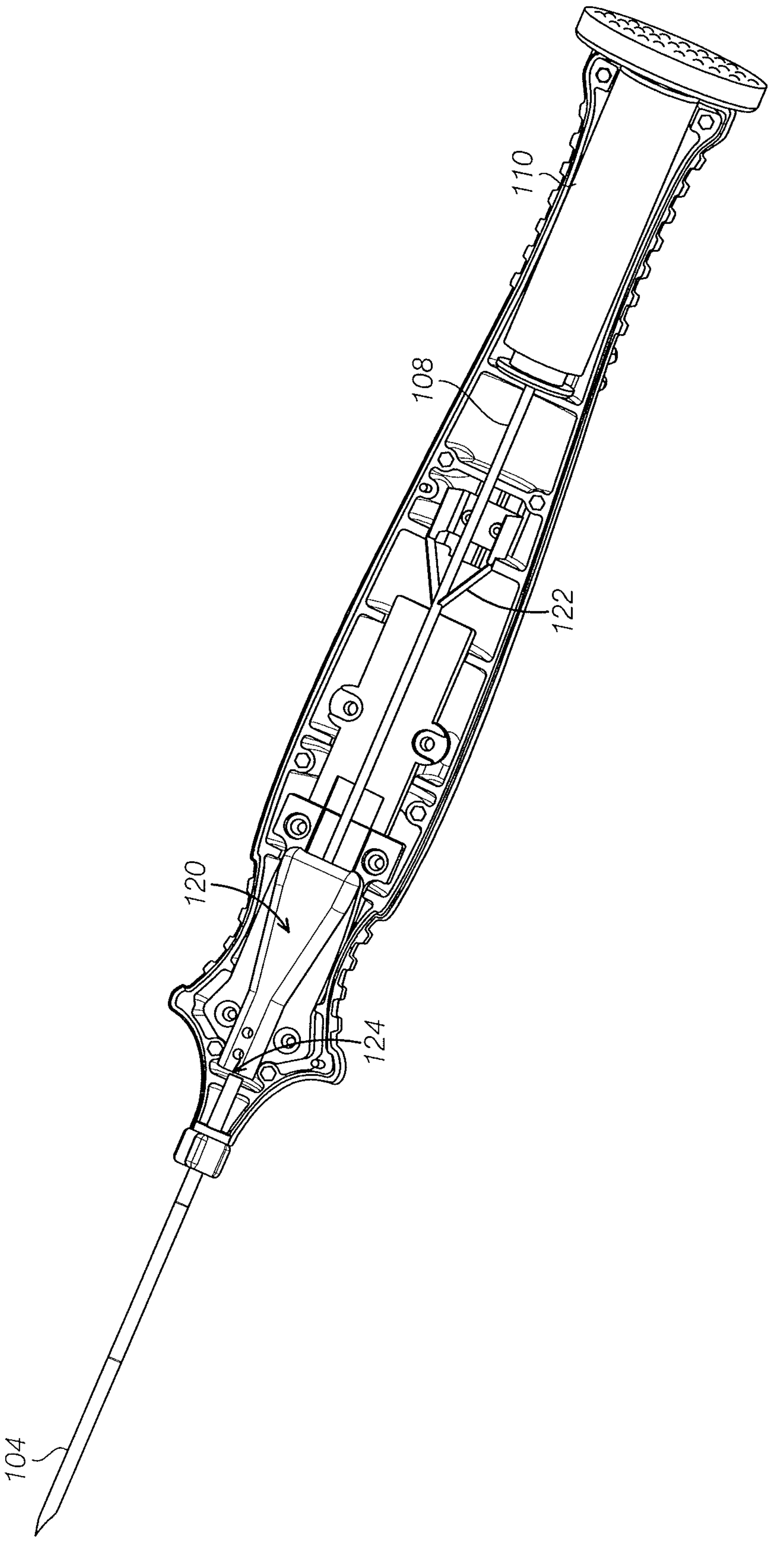
FIG. 6 shows a cross-sectional view of an implant delivery device for placing an implant into a body tissue.

FIG. 6 illustrates a cross-section view of the tool 100. The implant loading chamber 112 is in communication with the needle lumen 124 and adapted to load the nasal implant into the needle lumen 124. For example the implant loading chamber 112 can be adapted to move the nasal implant from a deployed configuration to a delivery configuration as the nasal implant is advanced into the needle lumen 124 from the implant loading chamber 112. The needle lumen 124 can have a substantially smooth inner surface to facilitate the delivery of the implant and withdrawal/retraction of the needle lumen relative to the implant after the implant has been delivered to the target location in the patient.

The implant loading chamber 112 can be in communication with an implant engagement surface 120 disposed between the needle lumen 124 and implant loading chamber 112. The implant engagement surface 120 can be adapted to engage with a first arm and a second arm of the implant 32 to move the implant from a deployed configuration and to a delivery configuration. In some embodiments the implant engagement surface includes a substantially smooth inner surface. The smooth inner surface can reduce the likelihood of a portion of the implant catching on the implant engagement surface as the implant advances towards the needle lumen.

The handle 102 includes an implant orientation indicator 116 configured to provide a visual indication of a plane formed by a first arm and a second arm of the nasal implant in the deployed configuration corresponding to the orientation of the implant within the needle lumen. The implant orientation indicator is designed so that the operator of the tool can quickly see the orientation of the tool and the corresponding orientation of the plane formed by the arms of the nasal implant in the deployed configuration. The implant orientation indicator extends from a portion of the handle such that the operator's hand does not cover or obscure the implant orientation indicator during use of the device. For example, the implant orientation indicators 116 can be located towards a distal end of the handle as shown in FIG. 5. The implant orientation indicator can include a first arm projecting from the handle in a first direction and a second arm projecting from the handle in a second direction. The first arm and second arm define a plane that is substantially similar to the plane formed by the first arm and the second arm of the nasal implant in the deployed configuration corresponding to the orientation of the implant within the needle lumen.

In some embodiments the delivery tool includes a push rod locking element proximal to the implant loading chamber configured to prevent further proximal movement of the push rod relative to the handle. The push rod locking element can be configured to prevent the push-rod from sliding outside of the interior portion of the handle. FIG. 6 illustrates a push-rod locking element 122. The illustrated push-rod locking element 122 is configured to engage with a notch 132 (FIG. 17) on the push-rod 108 to prevent further retraction of the push-rod 108 relative to the handle 102.

Figure 16:
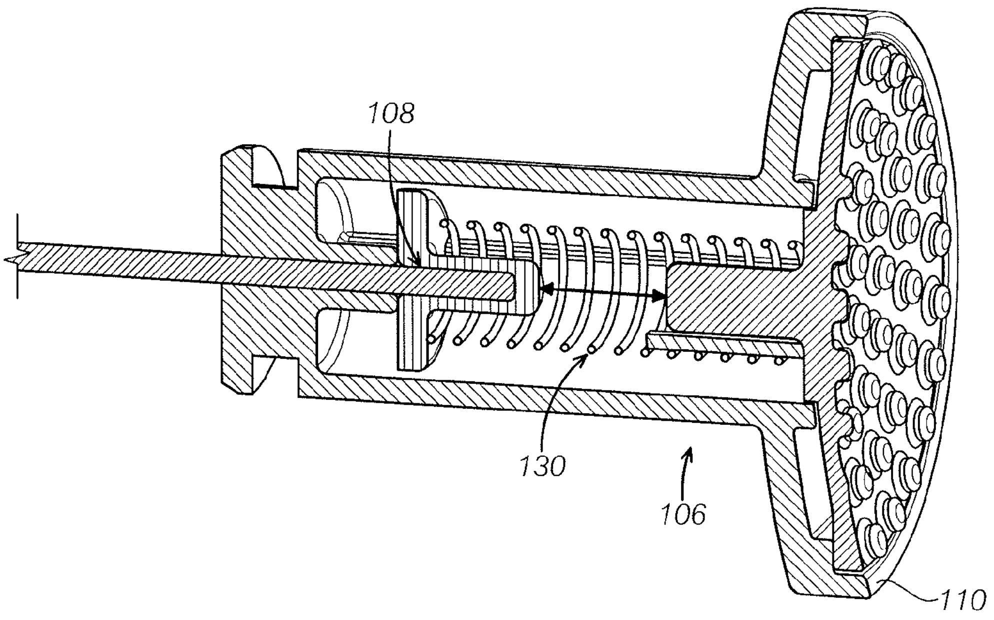
FIG. 16 shows an actuator for an implant delivery device.

The delivery tool actuator can include a push-rod and plunger assembly. In some embodiments a compression element can couple the push-rod to the plunger assembly. A compression element 130 is illustrated in FIG. 16 to couple the push-rod 108 to the plunger assembly 110. The compression element 130 can provide additional distal axial force on the implant to prevent the implant from retracting or sliding as the tool is removed or withdrawn from the patient.

Figure 7:
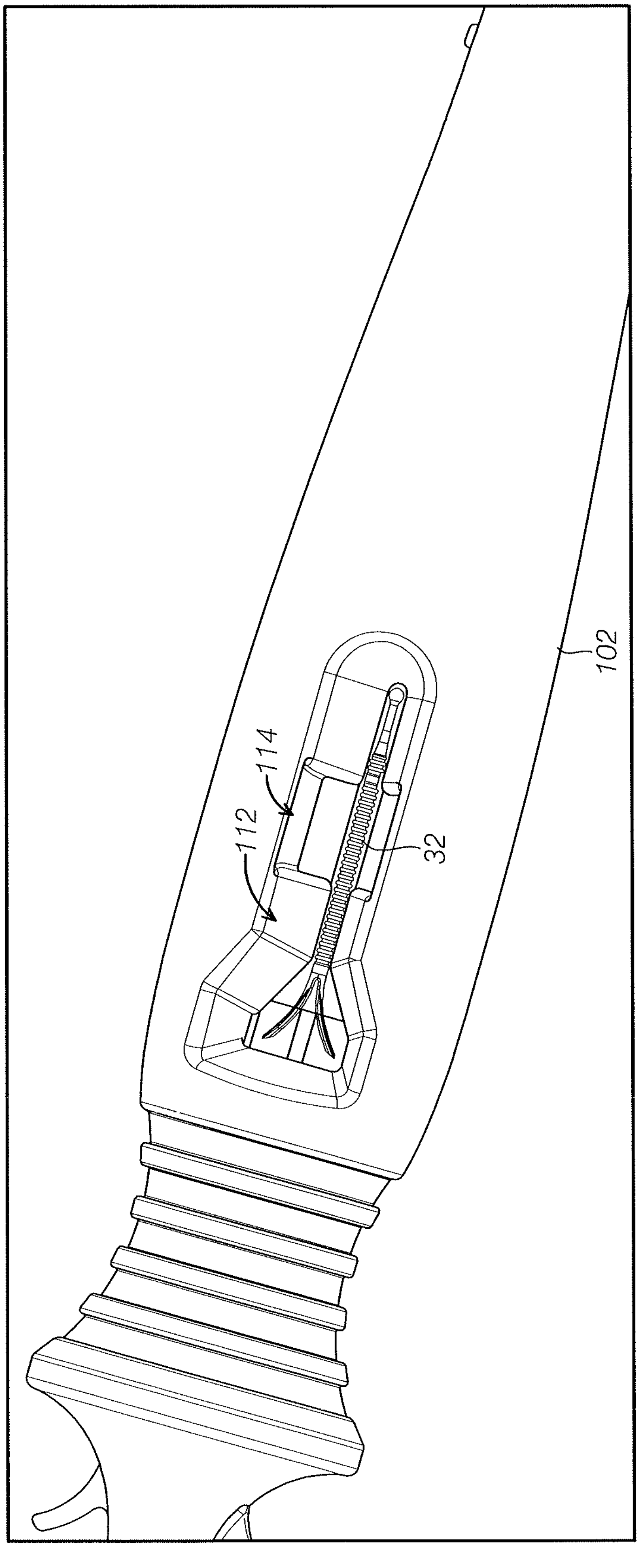
FIG. 7 shows an implant placed in an implant loading chamber of an implant delivery device.

FIG. 7 shows an implant 32 placed in the implant loading chamber 112 of the implant delivery device 100. The implant loading chamber 112 is configured to receive the implant 32 in the deployed configuration, e.g. with the implant arms spread open.

Figure 8A:
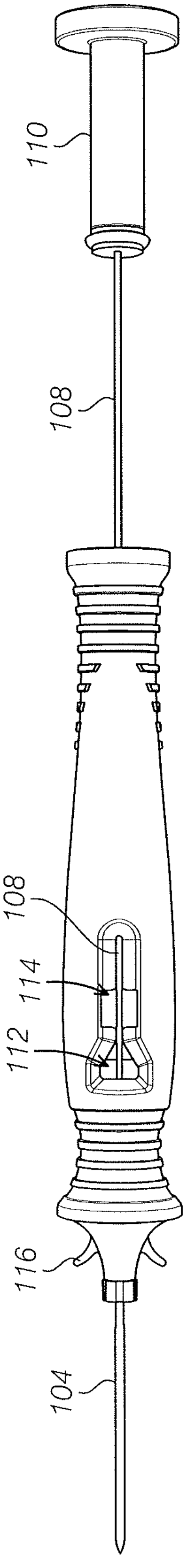
FIGS. 8A-8B show an implant delivery device, and an implant delivery device with an implant in the loading chamber, respectively, in accordance with some embodiments.
Figure 8B:
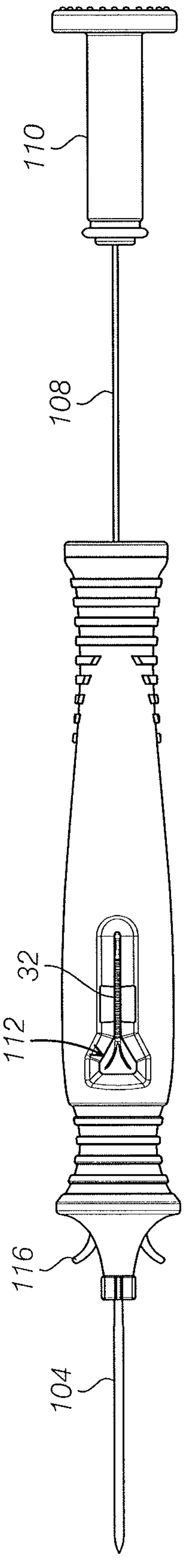

FIG. 8A shows the delivery tool 100 with the push-rod 108 and plunger assembly 110 in a retracted position such that the implant loading chamber 112 is not obstructed by the push-rod 108. FIG. 8B illustrates the implant 32 placed within the implant loading chamber.

Figure 9A:
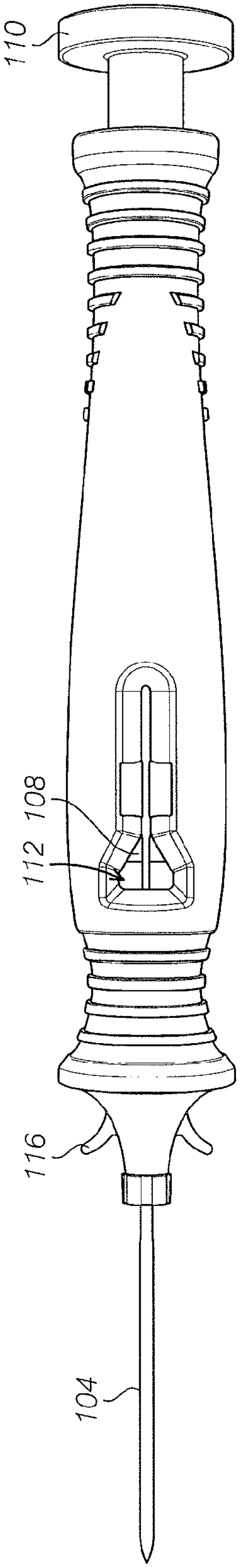
FIGS. 9A-9B show an implant delivery device with an actuator at various positions.

FIG. 9A illustrates the delivery tool 100 with the plunger assembly 110 and push-rod 108 advanced to push the implant from the implant loading chamber to within the needle lumen. FIG. 9A illustrates the implant at a pre-deployment stopping point with the implant contained within the needle lumen.

Figure 9B:
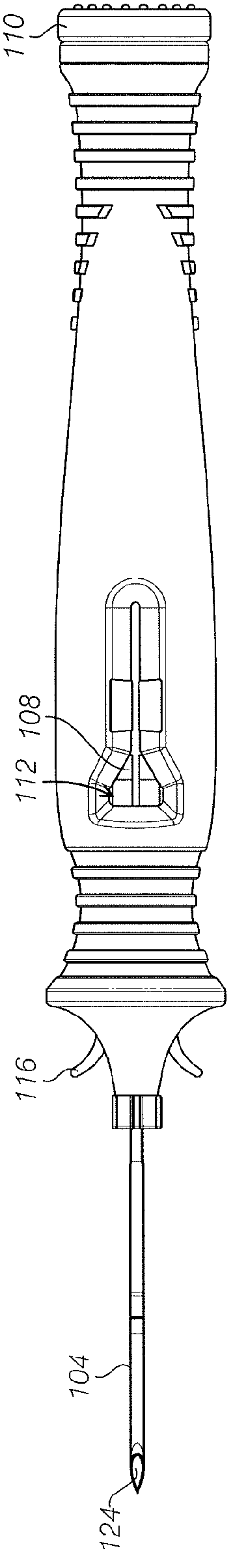
Figure 15:
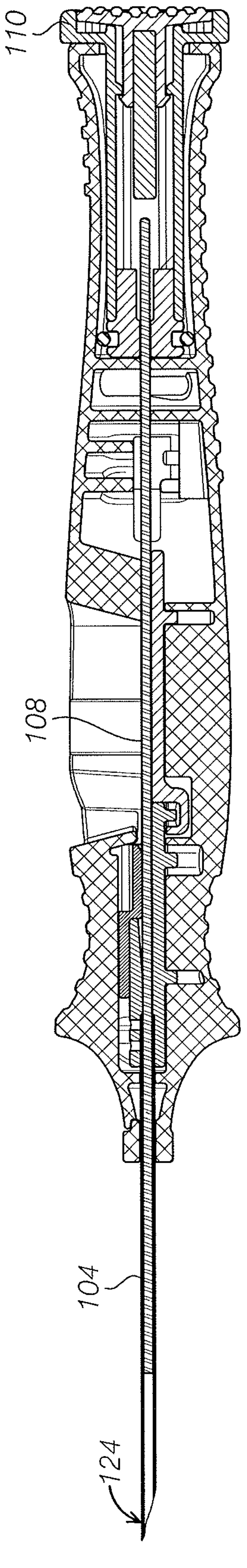
FIG. 15 shows a cross-sectional view of an implant delivery device for placing an implant into a body tissue.

FIG. 9B illustrates the push-rod 108 and plunger assembly 110 advanced relative to the configuration illustrated in FIG. 9A such that the implant would be pushed distally outside of the needle lumen 124. FIG. 15 shows a cross-sectional view of an implant delivery device with the push-rod 108 and plunger assembly 110 in the distally advanced position.

Figure 10A:
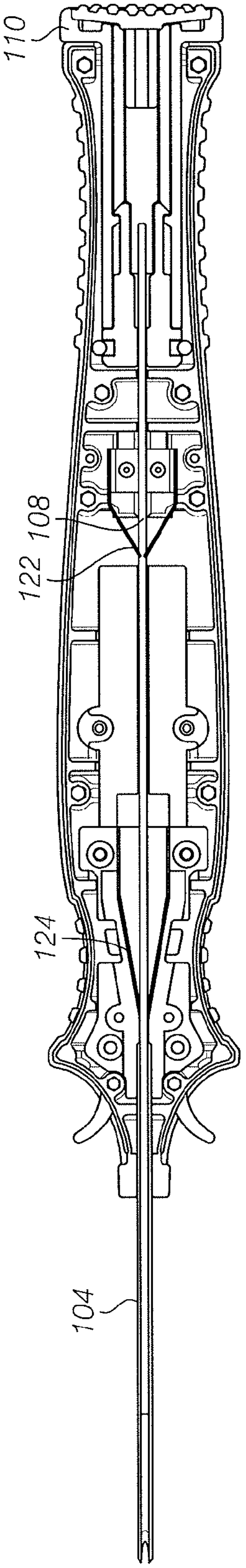
FIGS. 10A-10B show cross-sectional views of an implant delivery device with an actuator at various positions.
Figure 10B:
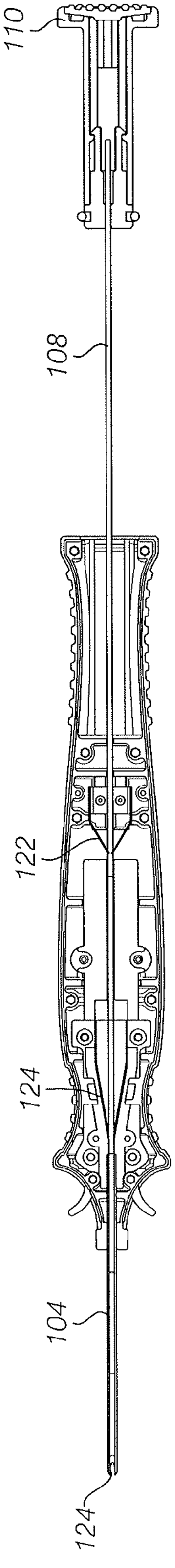

FIG. 10A illustrates a cross-sectional view of the tool 100 with the push-rod 108 and plunger assembly 110 in the distally advanced position. FIG. 10B illustrates a cross-sectional view of the tool 100 with the push-rod 108 and plunger assembly 110 in the retracted position such that the push-rod 108 is engaged with the push-rod locking element 122 and the implant loading chamber 112 is ready to receive and implant.

Figure 11:
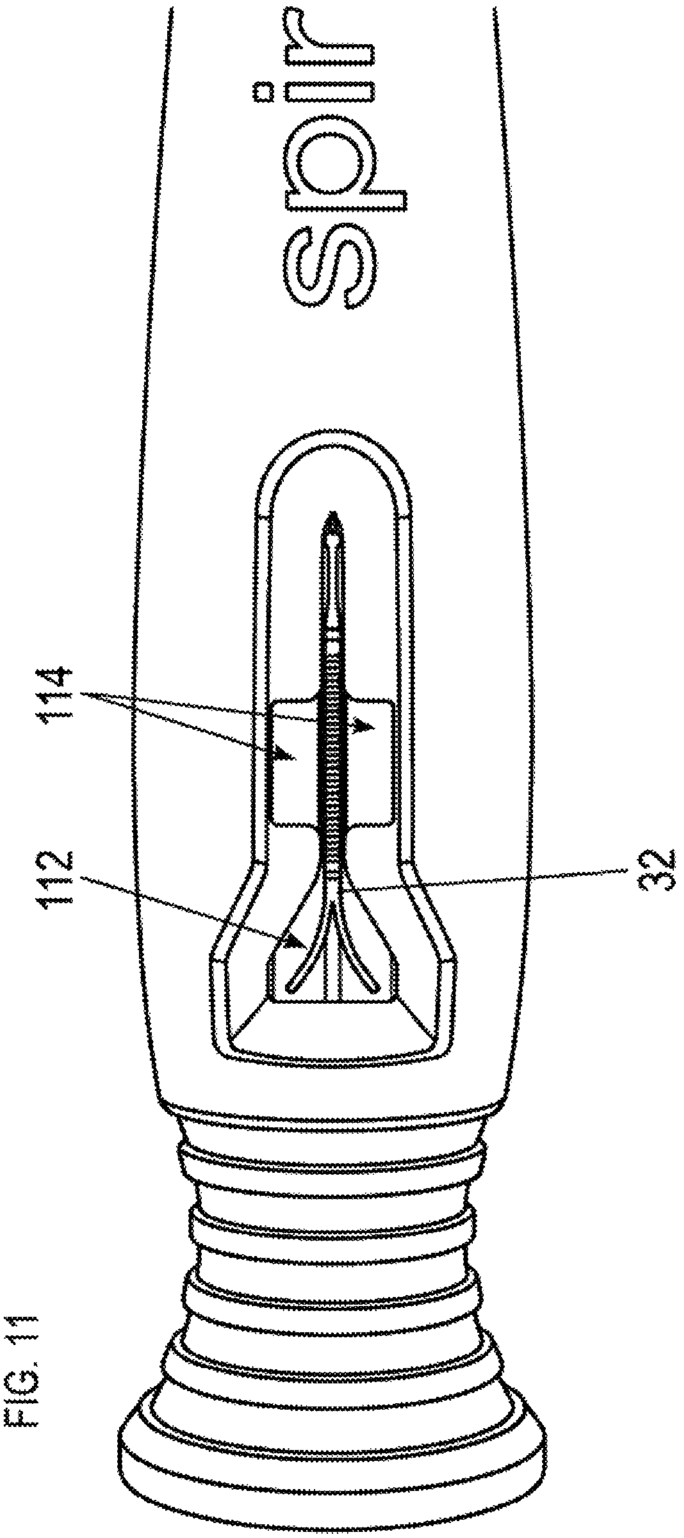
FIGS. 11-12 show an implant placed in an implant loading chamber of an implant delivery device.
Figure 12:
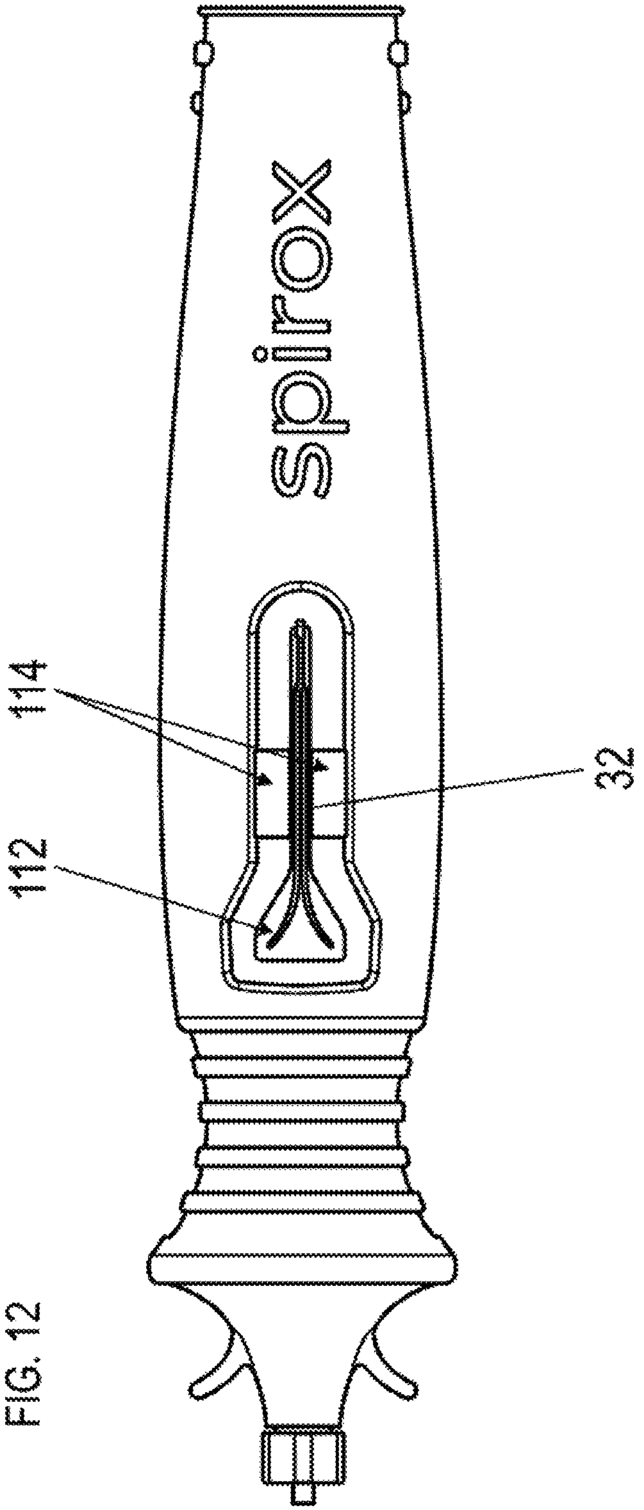
Figure 13:
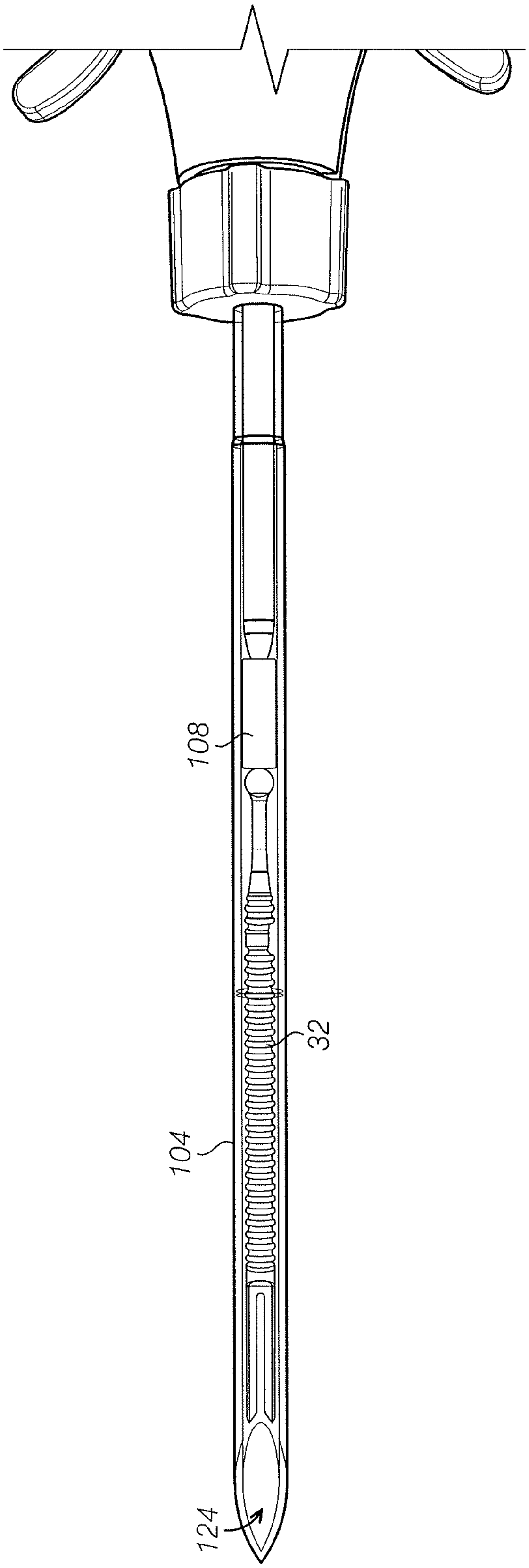
FIG. 13 shows a view of an implant within a needle lumen of an implant delivery device.
Figure 14:
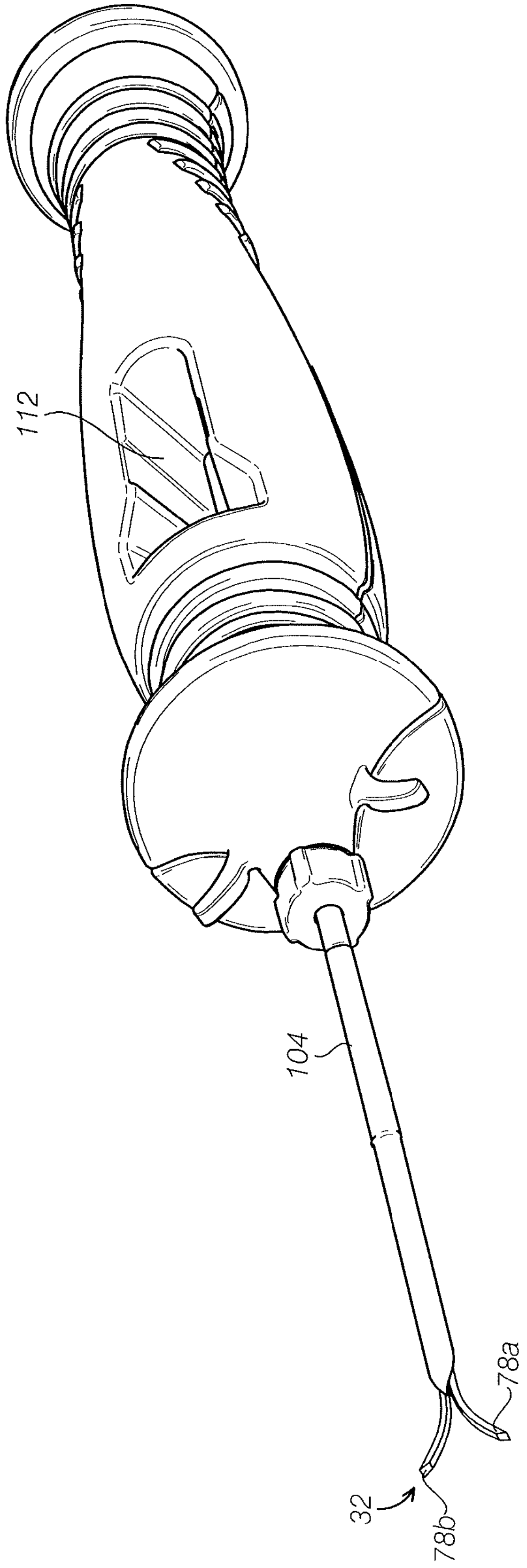
FIG. 14 shows a view of an implant extending distally from a needle lumen of an implant delivery device.

FIGS. 11-12 illustrate the implant 32 after being placed within the implant loading chamber 112. FIG. 13 shows the implant 32 within the needle lumen 124. The implant 32 is in a delivery/compressed configuration when it is located within the needle lumen 124. The push-rod 108 is shown distally advancing the implant 32 through the needle lumen 124. FIG. 14 illustrates the implant 32 as it extends distally past the distal end of the needle 104. The arms 78*a*, 78*b* of the implant 32 can move to the deployed configuration as the implant 32 exits the needle lumen 124.

FIG. 16 is an enlarged view of the actuator 106 showing the push-rod 108 engaged with the plunger assembly 110 via a compression element 130. The compression element 130 can provide a distal axial force on the push-rod 108 when initially retracting the push-rod after deploying the implant in the bodily tissue to decrease the chance of the implant migrating from the deployed location and position.

Figure 17:
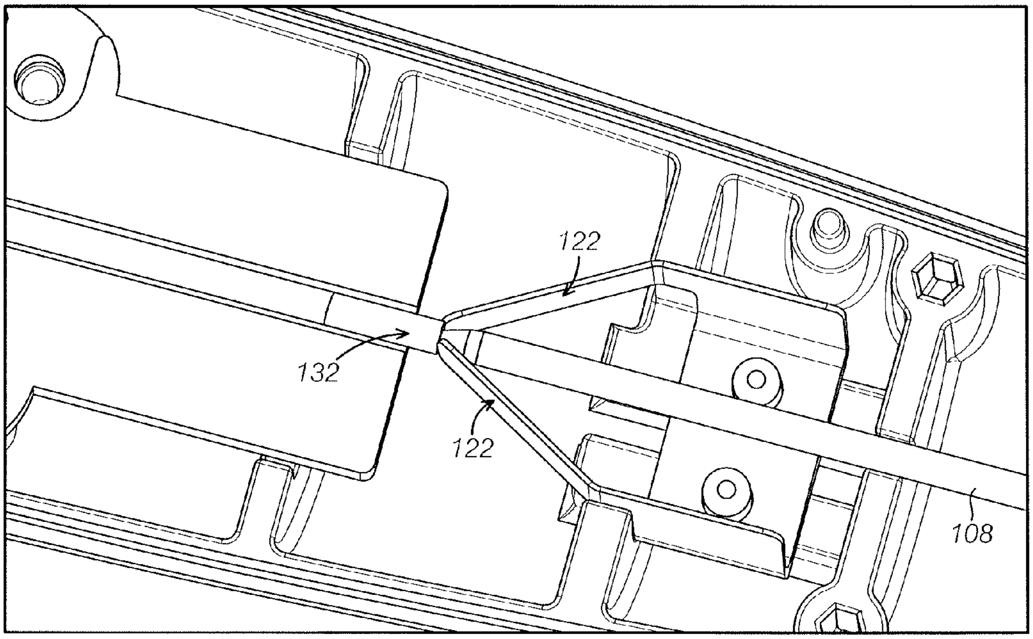
FIG. 17 shows a portion of a push-rod of an implant delivery device.

FIG. 17 is an enlarged view of a portion of the handle 102 showing the push-rod 108 engaged with the push-rod locking element 122. The push-rod locking element 122 can engage with the push-rod 108 at notch 132 to prevent further retraction of the push-rod 108 relative to the handle 102.

Figure 20:
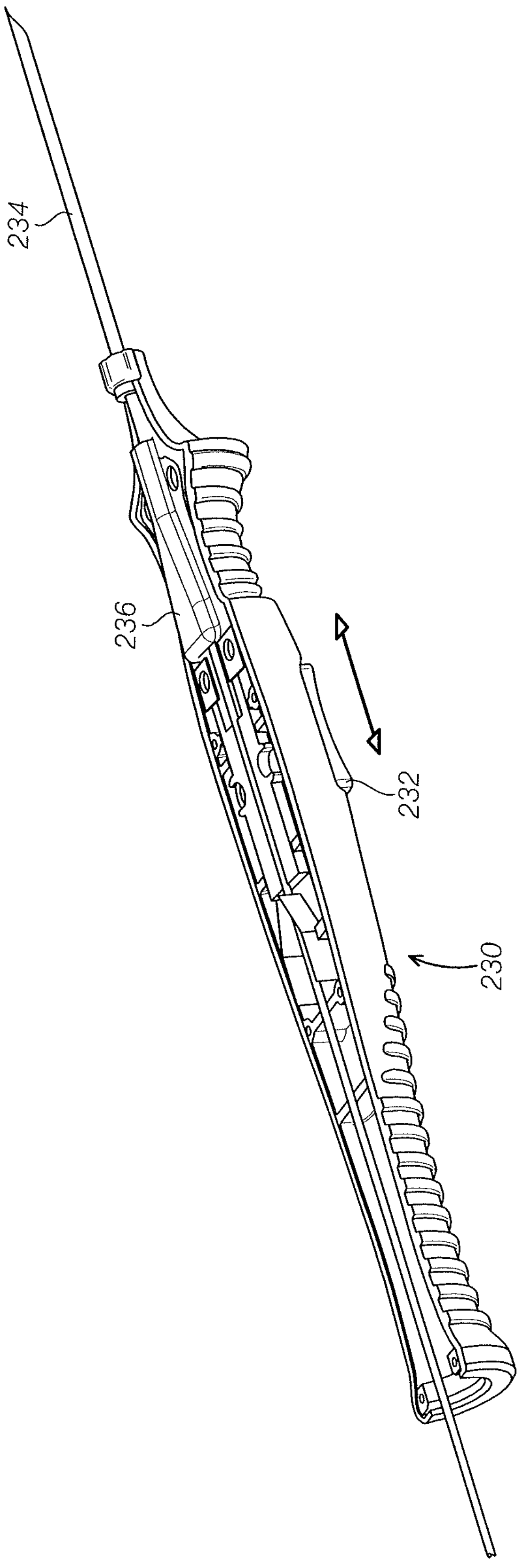
FIG. 20 shows an implant delivery device handle with a slider.

The delivery tool can be adapted for use with a variety of implant sizes and shapes. For example, the delivery tool can be adjusted to accommodate implants having different lengths and configurations. The implant loading chamber can be adjusted to allow passage of different implant sizes and shapes to within the handle of the delivery tool. One or more parts of the delivery tool can be adjusted between a plurality of positions in order to accommodate the different implant lengths. In one example the needle can be movable relative to the handle. The needle can be movable relative to the handle between a plurality of discrete positions. The plurality of discrete positions can correspond to a length of the nasal implant. For example, with a shorter implant the needle can be retracted proximally to effectively shorten the length of the needle extending externally from the handle. In one example a needle slider actuator is configured to move the needle between a plurality of discrete positions relative to the handle. FIG. 20 shows an implant delivery device handle 230 with a needle slider actuator 232. The needle slider actuator 232 can slide the needle 234 axially between the plurality of positions to accommodate the implant length. In some cases the slider can also move the implant engagement surface 236 and the needle 234.

Figure 18A:
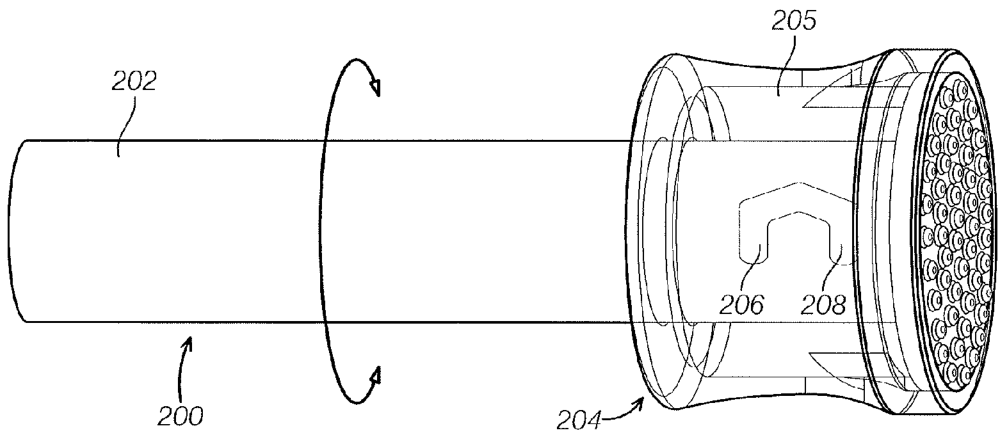
FIGS. 18A-18B show portions of an actuator for an implant delivery device.
Figure 18B:
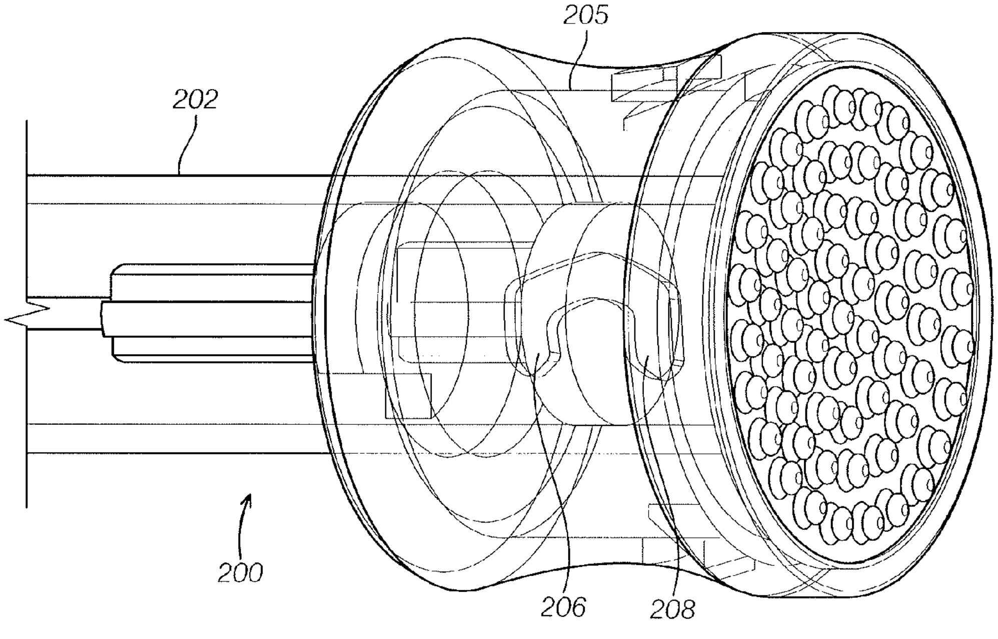
Figure 19:
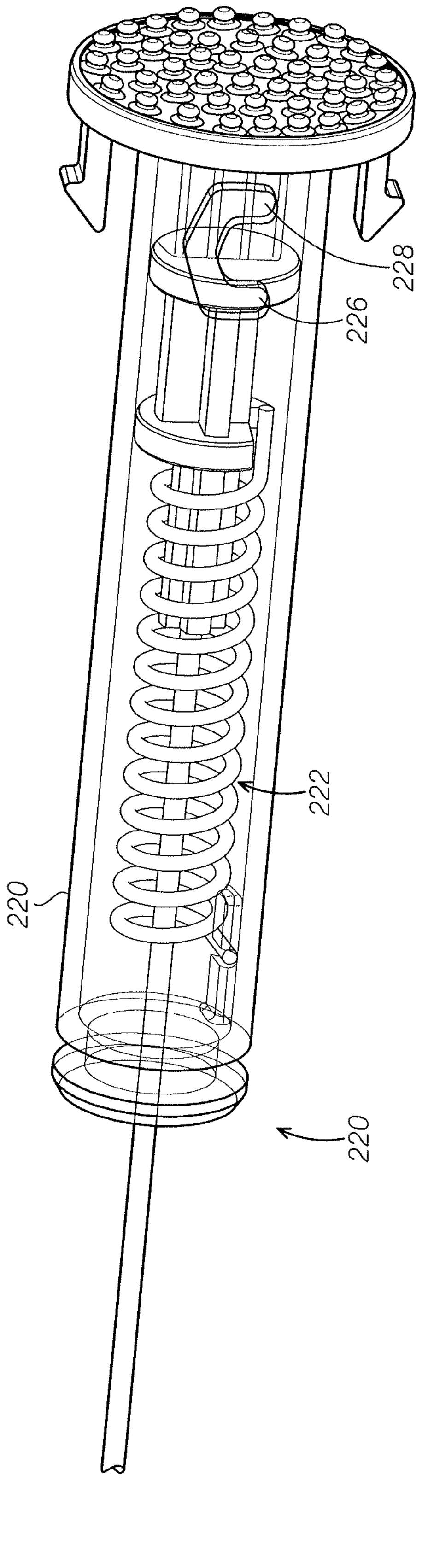
FIG. 19 shows a portion of an actuator for an implant delivery device.

In another example the actuator can be adjusted relative to the tool to accommodate the different implant lengths. For example, a length of the actuator can be adjustable between a first position and a second position. A length of the push-rod and plunger assembly can be adjustable between a first position and a second position by engaging the push-rod with a first locking surface on the plunger assembly and a second locking surface on the plunger assembly. FIGS. 18A-18B show an actuator 200 in two discrete positions. The push-rod 202 can be engaged with the plunger assembly 204 at two different positions 206, 208. The plunger assembly 204 knob 205 can be turned and then slid between the two positions 206, 208. The plunger assembly 204 can be locked or engaged such that the push-rod 202 and plunger assembly 204 length is locked during use. FIG. 19 shows an alternate configuration for the actuator 220 with the use of a torsion spring 222 to secure the plunger assembly 224 between the discrete positions 226, 228.

Figure 21:
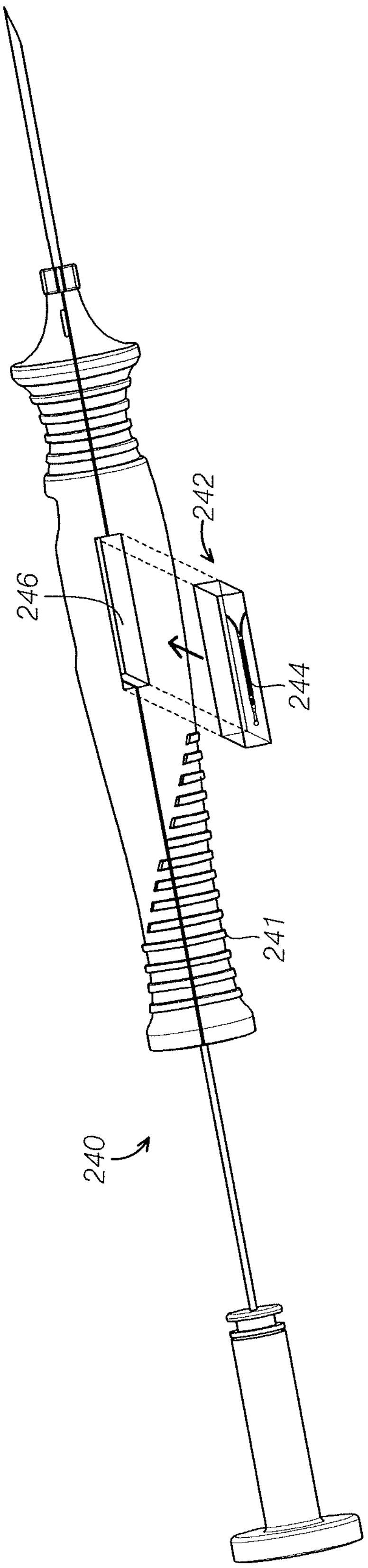
FIG. 21 shows an implant delivery device handle and cassette with an implant.

In some embodiments the delivery tool can be adapted to receive a cartridge containing one or more nasal implants in an implant loading chamber. The implant loading chamber can be adapted to receive a cartridge containing the nasal implant. FIG. 21 shows an implant delivery device 240 with a handle 241 and cassette/cartridge 242 with an implant 244. The cassette or cartridge 242 can include one or more nasal implants 244. The handle 241 can be configured to receive the cartridge 242 such that the nasal implant 244 can be advanced from the cartridge 242 to the needle lumen by the push-rod. In some cases the cartridge 242 can be configured to contain two or more nasal implants.

The cartridge can be adapted to be in communication with the needle lumen. The implant can move from within the cartridge directly into the needle lumen. In some cases the delivery device can include an implant engagement surface disposed between the cartridge and the needle lumen. The cartridge can also include an implant engagement ramp adapted to engage with a first arm and a second arm of the implant to move the implant between a deployed configuration and a delivery configuration. For example, the implant engagement ramp can urge the first arm and second arm of the implant into a compressed configuration such that the implant can be advanced from the implant engagement ramp into the needle lumen.

In some embodiments the handle can be adapted to receive the cartridge such that the cartridge engages with the needle to adjust a length of the needle relative to the handle. The delivery tool can be adapted to receive different cartridge sizes containing different implant sizes. The cartridge size can be designed to engage with the handle such that the length of the needle lumen is adjusted to work with the nasal implant contained within the cartridge. In another alternative the cartridge can be configured to adjust a relative distance between the actuator and the needle lumen by adjusting the actuator length.

A delivery tool may include an indicator configured to provide a signal about a status of the implant or the delivery tool. In some embodiments the needle includes substantially banded markings at various positions along the needle.

In some embodiments the needle of the delivery tool includes a low friction coating on an external surface of the needle. In some cases it can be difficult to penetrate portions of the nasal tissue. The low friction coating can be used to improve the needle penetration and movement relative to portions of the nasal tissue. The low friction coating can reduce drag forces between the tissue and needle during insertion and retraction of the needle in the bodily tissue. Generally, the low friction coating can be made out of a biocompatible and lubricious material that can adhere to the needle. Examples of materials that can be used for the low friction coating include: PTFE, silicone, and poly(p-xylylene) based polymers. One example of a suitable poly(p-xylylene) based polymer is available under the trade name of Parlyene™

The delivery tools can include an actuator register adapted to indicate a position of the actuator at which the nasal implant is at the distal end of the needle lumen. The actuator register can include a marking on the actuator or on the handle. The actuator register can be adapted to indicate a position of the actuator at which at least a distal portion of the implant has been moved out of the needle lumen.

Figure 22A:
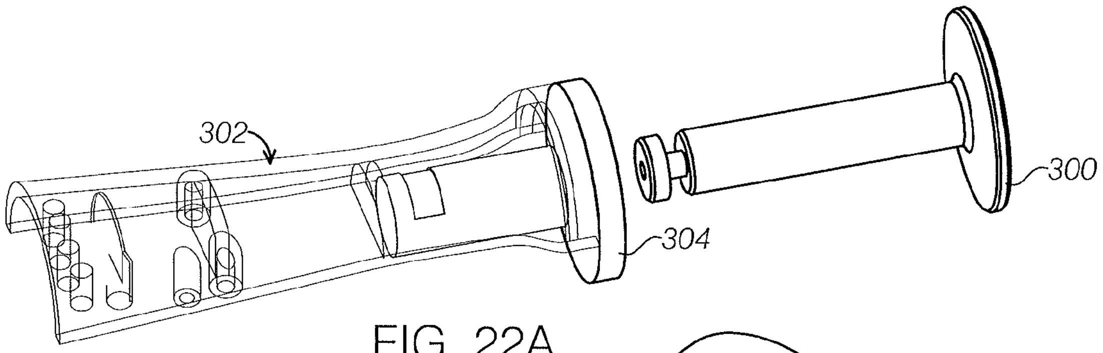
FIGS. 22A-22E show portions of an actuator for an implant delivery device.
Figure 22B:
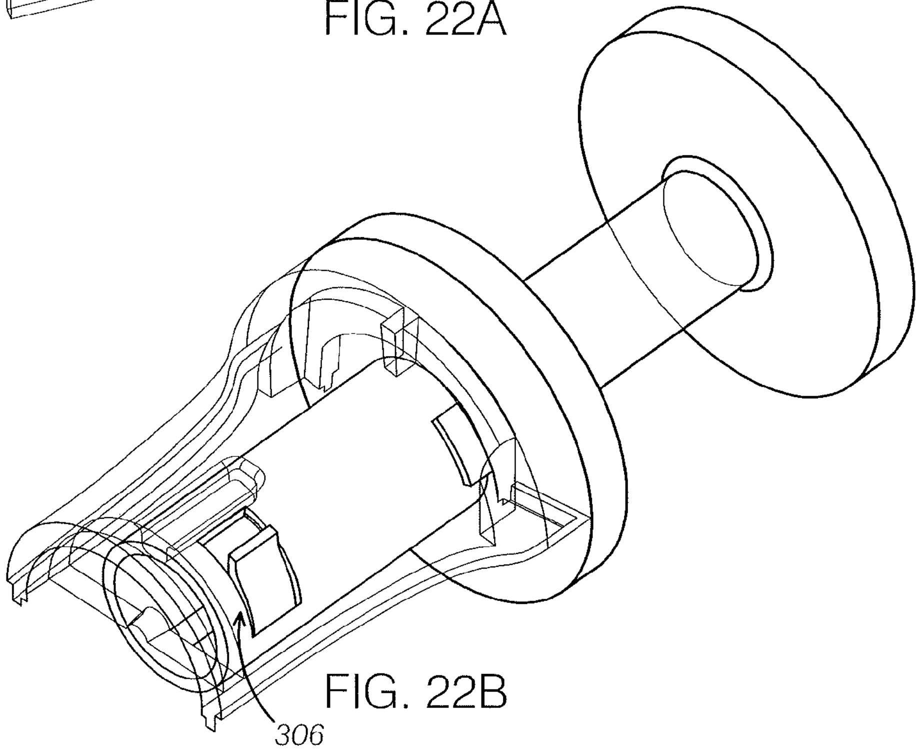
Figure 22C:
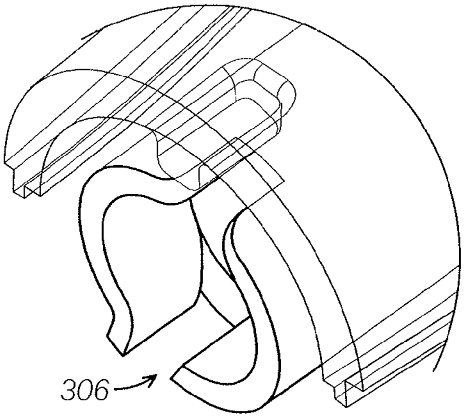
Figure 22D:
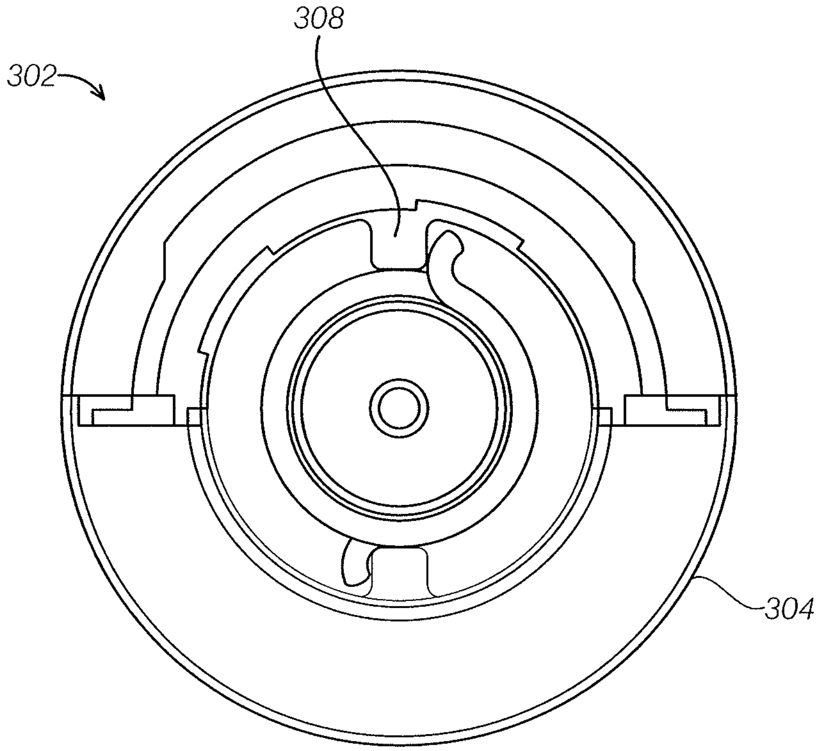
Figure 22E:
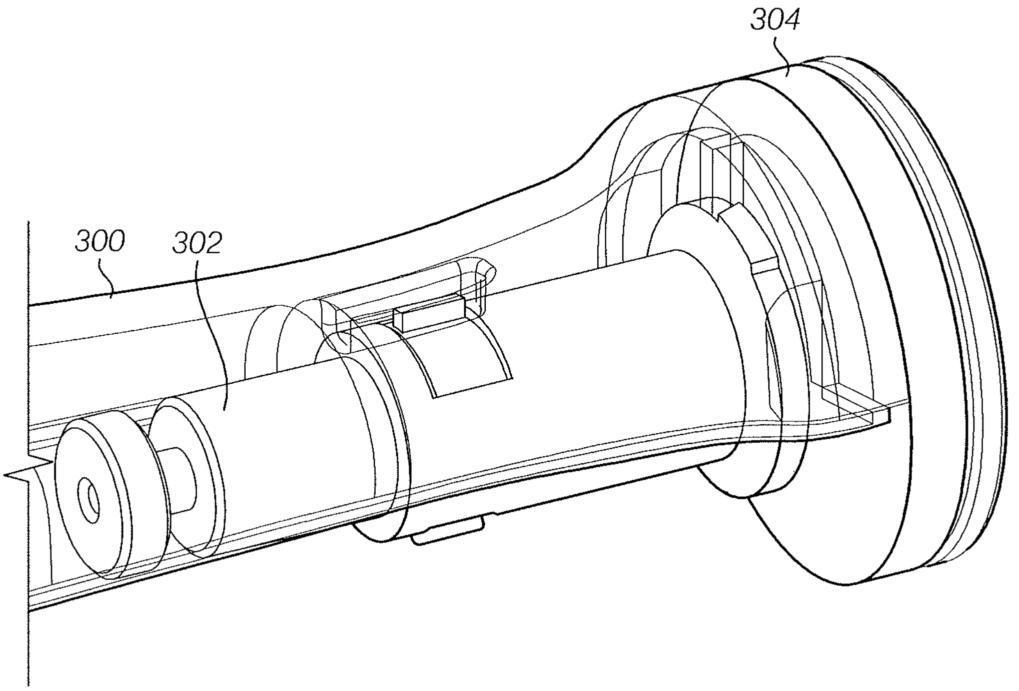

In some embodiments the actuator register is a stop element preventing further movement of the actuator. FIGS. 22A-22E show portions of an actuator for an implant delivery device in various configurations. FIG. 22A shows the plunger 300 prior to insertion within the delivery tool 302. The delivery tool 302 includes a tail sheath 304. The plunger 300 is received within the delivery tool 302 and engaged with the tail sheath 304. The delivery tool 302 includes a stop 306 that blocks the plunger 300 from advancing when the delivery tool 302 is in the implant load mode shown in FIG. 22B. FIG. 22B illustrates the plunger 300 in a first configuration relative to the tail sheath 304 with a stop 306 to allow for loading the implant. The plunger 300 can be stopped against a natural spring (FIG. 22C) or other stop. The plunger 300 can be turned or twisted (or the tail sheath 304 can be adjusted) to go from loading mode (FIGS. 22B-22C) to deploy mode (FIGS. 22D-22E). When twisted into deploy mode the spring feature or stop can be moved or forced open by feature 308 on the handle or other portion of the device to allow the plunger 300 to advance past the stop 306. In deploy mode the plunger 300 can be further advanced to deploy the implant.

In some embodiments the delivery tool can include a snap feature or mating pocket. Moving or snapping the snap feature into the mating pocket may create an audible "click", "snap" or other sound. A snap feature may be locked or held in connection with the mating pocket. A mating feature may move into a mating pocket when an implant is in a particular location in the delivery tool, or when an implant is partially or fully deployed. Some examples include the step of indicating with an indicator a location of an implant (e.g., a distal location, a deployment location) etc. A mating feature may be removed or unlocked from a handle, such as by manually depressing the snap feature in the pocket of the handle. This may be useful, for example, for releasing the plunger and re-loading an additional (second, third, etc.) into the delivery tool. An indicator may provide a signal that an implant is loaded (in place in the delivery tool), that part of an implant has been moved out of the needle (e.g., that a distal portion of an implant has been moved out of the needle), or that an entire implant may be moved out of a needle. A signal may be, for example, an audio signal (e.g., a beep, a buzz, a sound, etc.; a tactile signal (such as a vibratory signal), a visual signal (such as a colored or white light, a flash or a longer duration light signal), etc.

In some examples, a distal end of a needle may be sufficiently sharp to pierce nasal or facial tissue, such as any described herein. A sharp distal end may minimize nasal tearing. A needle may be any size, such as the size of a hypodermic needle as known in the art; e.g., outer diameter of 8 gauge, 10 gauge, 12 gauge, 14 gauge, 16 gauge, 18 gauge, 20 gauge, etc. A needle may be sized to fit between the mucosa, epithelium, muscle skin and cartilage or bone of the nose and face. In some examples, a needle may fit between a mucosa/skin and cartilage of the nose. A needle may be long enough to place an implant through tissue (e.g., at least 50 mm, at least 75 mm, at least 100 mm, at least 115 mm, at least 125 mm, or at least 150 mm. A distal end of the needle may include an opening adapted to fit an implant inside. The needle has a lumen which may be adapted to house or hold an implant. The lumen may have any cross-sectional profile, such as circular, non-circular, oval or ovoid, ellipsoid, triangular, square, rectangular, hexagonal, etc. In some variations, different regions of the lumen may have different cross-sectional profiles. A lumen with a non-circular cross-section may be oriented with respect to the handle of the delivery tool, and a handle of the delivery tool may control the orientation of the lumen (and control an implant oriented in the lumen). A handle may control the orientation of the implant during implant delivery. A lumen may have 1, 2, or 2, 3, 4, 5, or more than 2, 3, 4, or 5 different cross-sectional profiles. For example, a proximal portion may be circular and a distal portion may be non-circular. In some examples, a proximal lumen region may be circular, a middle lumen region may be non-circular (e.g., oval, ovoid, ellipsoid, or any other shape including those described above), and a distal lumen region may be circular. A lumen with a non-circular cross-section may have a major axis and a minor axis. An implant may be configured to engage or may be engaged with a lumen of a needle or with a lumen of a handle. An implant disposed in the handle lumen or needle lumen may have first and second arms at a distal end of the implant, the first and second arms may each have a proximal end fixed to the implant and a distal end not fixed to the implant, the distal end of each arm may be being biased to move away from a central longitudinal axis of the implant from a delivery configuration within the needle lumen toward a deployed configuration outside of the needle lumen, the first and second arms each comprising a beveled surface (e.g., an outer beveled surface) engaged with an inner surface of the needle lumen on opposite ends of the major axis. Some examples include maintaining a known orientation between an implant and a lumen (needle) during the inserting step.

A guide may provide guidance to an implant, but in general provides guidance to an actuator. A guide and an actuator may have complementary shapes. For example, a guide may be a trough and an actuator may be a rod that fits partway inside the trough. In general, part of an actuator will sit above a guide when in place in a guide such that the actuator is able to act upon (move) an implant through the delivery tool.

The actuator can include one or more markings. The marking may indicate the position of the actuator relative to the delivery tool or implant. For example, marking may be configured to indicate an implant is in the desired location for implant deployment in a tissue, a distal end of an implant is at a distal end of a delivery tool, an implant is in a partially deployed position, an implant is fully delivered (deployed) into a tissue, etc. A marking may be useful to indicate that an implant is in a position, is ready to be deployed (in a pre-deployment position), is partially deployed, or fully deployed. For example, a marker may indicate when the arms of an implant (the fork region) has been deployed and expanded, and the remainder of the implant is in the delivery tool. A marking may be any type of marking, e.g., a line, multiple lines, a thick line, a protrusion, a ring, a color, a fluorescent marker, etc. as long as it provides an indication of the location of the actuator or implant (e.g., relative to the delivery tool). The delivery tool is may be withdrawn from the tissue to finish deploying the implant (e.g., to move the non-arm containing portion of the implant (e.g., implant body) out of the tissue, such as by withdrawing the needle while holding the implant in place (in the tissue) with the actuator. An actuator may include 1, 2, 3, 4, 5, or more than 5 markings for any reason, such as those just described. Additionally, an actuator may have different markings corresponding to different length implants. Actuator may further include a stop mechanism to stop the actuator from traveling further in the delivery tool.

Systems are also provided including the delivery tools described herein and a one or more nasal implants. Systems are also provided including the delivery tools described herein and a cartridge containing the nasal implant. The cartridge can contain two or more nasal implants. In some embodiments the cartridge can include an implant engagement surface configured to move the implant to a delivery configuration.

As mentioned above, an implant may be placed in a minimally invasive way utilizing a small opening in the body to minimize pain and scarring. It may be advantageous however for an implant to be larger than the small opening if, for example, the region of tissue to be treated is larger than the small opening in the body. In such a case, an implant may be placed through the opening in a contracted configuration and may be expanded during or after placement in the body. Additionally, an implant that is expanded during insertion may exert a force on tissues (e.g., which may help hold the implant in place). In some variations, a delivery tool may be configured to accept an implant that is in an expanded configured, contract the implant so that it would fit through the small opening in the body, and then deliver the implant to a body tissue. The implant may be delivered while the implant is in the contracted configuration. An implant may be delivered in an expanded configuration or may be expanded during delivery. A delivery tool may include a loading chamber for loading an implant in an expanded configuration into a delivery tool and one or more shaping chambers to change the shape of the implant. A delivery tool may include an implant loading chamber communicating with the needle lumen and adapted to load a nasal implant into the needle lumen.

A loading chamber may generally have a rectangular shape, but could instead have an ovoid or another shape as long as it is able to accept an implant (e.g., in an expanded configuration) and to allow an implant to be moved through the loading chamber (e.g., by a plunger/actuator). A loading chamber may be enclosed on the top (have a roof), but generally will be open on the top to allow insertion of the implant. A loading chamber has a floor and generally has first and second lateral walls (sides) and proximal and distal walls (ends), with the proximal and distal walls each connected (e.g., at either end) with the first and second lateral walls. The proximal and distal walls may each have an opening with the proximal wall opening configured to allow a plunger/actuator to enter the loading chamber and a distal wall opening in open communication with the needle lumen. A proximal wall of loading chamber may have an opening configured to allow the implant or plunger of an actuator to pass through. An implant may be placed (dropped) into the loading chamber from the top so that is lies on the floor of the chamber.

Shaping the implant as described using a loading chamber, shaping chamber/implant engagement surface and needle may instead be performed in other ways as long as the implant is moved from an expanded configuration to a contracted configuration in the delivery tool. For example, an implant delivery tool may have only a loading chamber and the loading chamber may shape an implant as described above without use of shaping chamber; the implant may travel directly from the loading chamber to the needle. An implant delivery tool may have multiple shaping chambers and each may partially change the implant configuration. A shaping chamber may be ovoid or may be rectangular, etc.

An implant may take on a different shape or different configuration as it is implanted (during implantation as it moves out of the needle and into the body tissue). Implant 32 may move from a delivery configuration towards a deployment configuration during implantation in a tissue. An implant may move from a contracted or compressed configuration to an expanded configuration by one or more distal arms moving away from a central longitudinal axis of the implant. The arms (e.g., distal ends) of the arms may be biased to move away from a central longitudinal axis. The arms may move go straight out, but in general will diverge away from a central longitudinal axis such that the distal ends of the arms are bent. Tissue may be trapped between the arms. Diverging arms may help distribute forces across a wider area of tissue. In nasal tissue, tenting and distal migration may be prevented or minimized. Diverging arms may also keep the implant in place as the needle or delivery device are removed. Bevels may help the arms diverge. Arm movement may be aided in moving through tissue by a bevel on a radially inward surface of the distal end of the arm. The bevel may cut through tissue and guide the arm through the tissue. Although shown with an implant with two arms with bevels, an implant may have no bevels, a single bevel, a bevel on each arm, two bevels on each arm, etc. and may have 0, 1, 2, 3, 4 or more arms. The implant may be advanced (pushed) into body tissue by an actuator/plunger.

An implant in a contracted position may be deployed directly into tissue to move from a contracted configuration to a delivery configuration, but generally may be oriented before deployment. An implant may be oriented in the delivery tool handle, but generally is oriented in the needle. An implant may be oriented by a non-circular lumen (in either the delivery tool handle or in the needle). A non-circular lumen with a major axis and a minor axis may allow the arms of the implant to diverge (slightly) in the outward direction of the major axis (and away from the central longitudinal axis), thus orienting the implant (via the arms) in the direction of the major axis. This may occur, for example, as the plunger is moving the implant through the implant tool handle but generally will happen as the implant is moving through the needle. In some examples, after the implant is oriented, the needle may have a circular cross-sectional region and the implant may travel through the circular cross-sectional region, but maintain its orientation. For example, the distance travelled through the circular cross-sectional region may be relatively short.

An implant may move from a delivery configuration within the needle lumen toward a deployment configuration outside the needle lumen. As the implant exits the distal end of the needle, the arms may travel away from each other (diverge). The implant may be fully deployed before the implant tool is removed away from the implant or the implant may be partially deployed (e.g., the arms may be deployed but the rest of the implant may be disposed inside the needle of the delivery tool, and, once the arms are deployed, the needle may be removed away from the implant and away from the tissue to leave the implant in place). In some examples, the actuator may push the implant further into tissue (aided by inner bevels on the arms to move the arms through the tissue). In other examples, the actuator may hold the implant in place as the delivery tool is removed away from the implant and the actuator, and then the actuator is removed, leaving the implant in place in the tissue. The implant may move through tissue aided by the inner bevels that cut through tissue and/or by the biased arms attempting to return to their unbiased configuration. An implant may move from a deployment configuration towards a delivery configuration as it exits the distal end of a delivery device.

In some embodiments advancing the implant includes pushing the implant distally such that the first arm and second arm of the implant each engage the tissue thereby moving away from the central longitudinal axis of the implant. In some embodiments advancing the implant can include retracting a portion of the delivery tool, such as the needle, to allow the first arm and second arm of the implant to self-expand such that the arms move away from the central longitudinal axis of the implant. In some cases advancing can include a combination of pushing and retracting. For example, advancing the implant can include pushing the implant distally and retracting a portion of the delivery tool such that the first arm and second arm each engage the tissue thereby moving away from the central longitudinal axis of the implant. The first arm and second arm of the implant can each form an incision path as the implant engaged with the tissue. For example, advancing the implant can include the first arm forming a first arm incision path with the first arm incision path having a longitudinal axis that is offset from a longitudinal axis of the delivery tool. Advancing can also include the second arm forming a second arm incision path with the second arm incision path having a longitudinal axis that is also offset from a longitudinal axis of the delivery tool. The longitudinal axis formed by the first arm incision path and the second arm incision path can include a curved or arced shape. The first arm incision path and second arm incision path can form an angle that is less than 180 degrees. Advancing the implant can also include the first arm and second arm each engaging a portion of tissue located between the first arm and the second arm.

Methods for using the delivery tools to deliver the implants disclosed herein are also provided. The methods for supporting a tissue section of a patient's nose can include inserting a needle of a delivery tool into tissue of the nose. The delivery tool can include a handle portion with the needle extending distally from the handle. The needle can include a needle lumen. The handle can include an implant loading chamber adapted to receive an implant. The delivery tool can also include an actuator adapted to move the implant along the needle lumen and out of an opening at the distal end of the needle. The method can include advancing the implant distally from the needle lumen to place a distal end of the implant within the nasal tissue. The implant can include a first arm at a distal end of the implant and a second arm at the distal end of the implant. Advancing the implant distally can include the first arm moving away from a central longitudinal axis of the implant during the advancing step and the second arm moving away from the central longitudinal axis of the implant. The methods can include withdrawing the delivery tool to dispose a central portion of the implant within the nasal tissue and supporting the tissue section with the implant.

Advancing the implant can include pushing the implant distally such that the first arm and second arm each engage the tissue thereby moving away from the central longitudinal axis of the implant.

The methods can include loading the implant into the implant loading chamber of the delivery tool. The methods can include loading the implant into the implant loading chamber using tweezers. The methods can include loading a cartridge containing the implant into the implant loading chamber.

The methods can include retracting a push-rod of the actuator to a proximal locking point prior to loading the implant in the implant loading chamber.

The methods can include adjusting a length of the needle extending from the handle prior to loading the implant. The methods can include sliding the needle relative to the handle by moving a slider on the handle coupled to the needle to move the needle between a plurality of discrete positions relative to the handle. The methods can include adjusting a length of the push-rod and plunger assembly prior to loading the implant.

The methods can include advancing the implant from the implant loading chamber into the needle lumen. The delivery tool can include an implant engagement surface disposed between the needle lumen and implant loading chamber with methods including advancing the implant from the implant loading chamber through the implant engagement surface and into the needle lumen. The loading step can include loading the implant into a proximal end of the needle and advancing the implant to the distal end of the needle prior to the inserting step. The loading step can include collapsing the first arm and second arm of the implant prior to entering the proximal end of the needle.

The methods can include advancing the actuator to a locking point followed by unlocking the actuator prior to advancing the implant distally from the needle lumen to place the distal end of the implant within the nasal tissue.

The inserting step can include inserting a distal end of the needle into tissue of the nose. The methods can also include maintaining a known orientation between the implant and the needle during the inserting step. Maintaining the known orientation between the implant and the needle can include engaging the implant with a portion of a lumen of the needle having a non-circular cross section.

The methods can include continuing to provide a distal axial force on the implant with the push-rod and compression element while initially withdrawing the delivery tool.

When in place in a body tissue, such as in a nasal tissue or any other type of tissue in the body, a bone or other structure may provide cantilever support to an implant. For example, extending an implant for supporting a nasal valve beyond the edge of the maxillary bone may provide cantilever support. Implant 32 may leverage one or more forces between the different portions of the implant to provide a force to alter or support a tissue in need of alteration or support. Implant 32 may leverage force from one or more underlying structures (e.g., a bony structure such as a maxillary or nasal bone, an accessory, upper, or lower cartilage) to a structure needing support (e.g., an accessory, upper, or lower cartilage such as a caudal region of an upper lateral cartilage). Linking an upper cartilage and lower cartilage will support or strengthen the nasal valve and may improve nasal appearance or breathing or reduce snoring or other problems. As discussed above, the upper lateral cartilage 11 and lower lateral cartilage 16, along with the nasal septum, and the inferior turbinates, border the nasal valve. Implant 32 acts to support or alter the nasal valve. In a particular example, a force may be leveraged by the implant to alter or support a caudal (lower) region of an upper lateral cartilage and thereby alter or support an internal nasal valve and internal valve angle. A valve angle may be increased, decreased or may stay the same in response but in general will stay the same or be increased. Although the overlying skin and tissue of the nose have been removed in this figure, they may provide force and may hold the implant against the underlying tissues anywhere along its length, such as holding the implant over the maxillary or nasal bone, or over its entire length. Nasal bone 4 may exert a force on implant 32. An implant may behave as a lever to provide support to a structure. A structure such as a bone (e.g., a nasal or facial bone), cartilage, or other body structure may place a force on an implant to thereby provide support along the length of an implant and provide support to a body structure, such as a nasal valve. For example, a nasal or maxillary bone may provide force to upper lateral cartilage 8 and lower lateral cartilage 16.

In some variations, an implant is a biocompatible implant useful for nasal valve repair. An implant may be used to strengthen a nasal valve in a patient's nose. An implant may support the cartilage and help resist or reduce movement of the cartilage during inhalation, thereby keeping the patient's airway open. While implant 32 in FIGS. 2A-2B is apposing or in proximity to particular structures in the cartilage and bony framework layer of a patient's nose, as well as to the overlying muscle/skin, an entire implant or one or more regions of an implant may be apposed to or placed in proximity to any (body) cavity, structure, or tissue in a patient's body. For example, a projection (arm) or other protrusion, or part of an arm or other protrusion, a central region, part of a central region, a distal end, a proximal end, a strain relief portion, a feature, a ridge, etc. may be apposed to or placed in proximity to any (body) cavity, structure, or tissue in a patient's body. In some variations, an implant or a region of an implant may be apposed to or placed in proximity to one or more of any cavity, structure or tissue, such as a facial or nasal bone, cartilage, connective tissue, fascia, fat, respiratory epithelium, squamous epithelium, squamous epithelium of the nasal cavity, ligament, muscle, mucous, skin, (alar) fibrofatty tissue, a blood vessel, mucosa, nasal mucosa, a frontal bone, a lacrimal bone, a maxilla bone (e.g., an anterior nasal spine, a frontal process), a nasal bone, a vomer bone, a nasomaxillary suture, a nasofrontal suture, an accessory nasal cartilage, an upper lateral cartilage (including a cranial border, a caudal border or a central region of the upper lateral cartilage), a lower lateral cartilage, a major alar cartilage (e.g., lateral crus, medial crus), a minor cartilage, a septal cartilage (e.g., a lateral process, a nasal septal cartilage), etc. An implant may be apposed to or placed in proximity to one or more other implants or synthetic structures. An implant apposed to or in proximity to a (body) cavity, structure, or tissue may act upon it (e.g., support it, place a force on it or resist a force from it, act as a fulcrum for a force from it, etc.) or may not act upon it. For example, part of an implant may lie across a tissue, but not have a substantial interaction or impact on that tissue. An implant be placed overlying or underlying one or more of the above mentioned tissues. An implant may be placed in any orientation relative to these tissues and may lie substantially parallel, perpendicular or skewed relative to a long or short axis of a cavity, a structure, a tissue or another implant. In some examples, an implant is placed within a nasal tissue. In some embodiments, an implant is located partially within a nasal tissue and partially within a surrounding tissue (e.g., a maxilla). An implant may be attached (e.g., with an adhesive, a suture, a screw, etc.) to a structure, a tissue, or another implant (such as those described herein) or may lie close or in contact with a structure, a tissue, or another implant (such as those described herein). An implant may be placed so that a proximal tip of the implant has sufficient clearance from the nostril rim for insertion through mucosal tissue. An implant may be held in place by a force between the implant and a structure, a tissue, or another implant such as a compressive force. An implant may be held (at least partially) in place by forces on the implant from an overlying layer. In some particular examples, a distal end of a nasal implant is held (at least partially held) in place against the maxilla and/or nasal bones and/or nasomaxillary suture by (the tightness of) the overlying skin and muscle pressing the implant against the bone or suture.

Figure 3A:
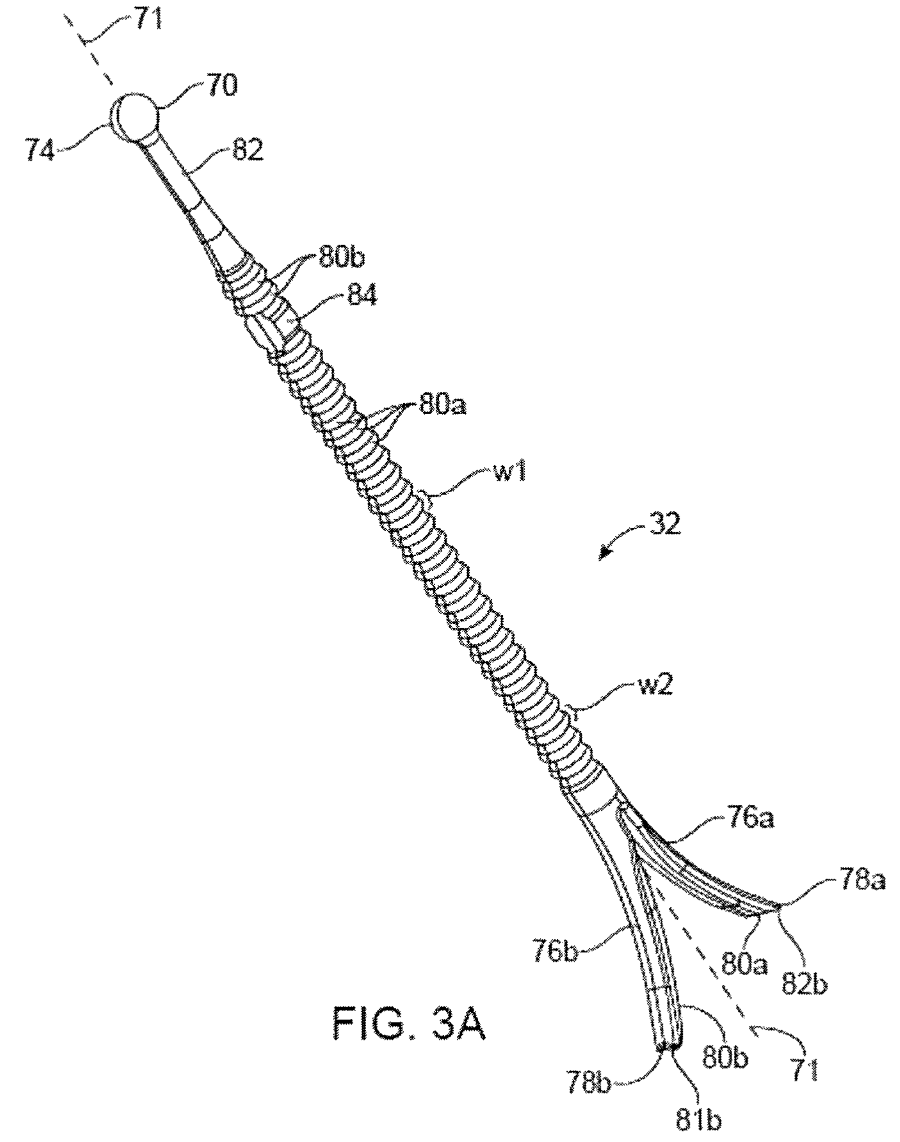
FIGS. 3A-3B show an implant with arms.

FIG. 3A shows an implant for acting on a body tissue with a generally longitudinal body having first end 70, second end 72, and a central portion disposed between the first end and the second end. The implant defines a central longitudinal axis 71. In some examples, the first end of the implant is in a proximal location of an insertion site in a tissue. Second (or distal) end 70 of implant 32 has first arm 76*a* and second arm 76*b*, each arm having a proximal end fixed to the body and a distal end not fixed to the body.

In some variations, an implant is adapted to have or take on different configurations. For example, an implant may have a contracted configuration and an expanded configuration. An implant may be able to take on a (continuous) range of configurations in between the contracted and expanded configurations. In some cases, an implant may be able to be held in any of these configurations. A contracted configuration may be a delivery configuration and may be useful for delivering an implant, such as moving the implant through an implant delivery device and placing it into a body tissue. A contracted implant may be small enough to readily fit into a relatively small delivery device. An implant in an expanded configuration may be a deployed configuration and may be useful, for example, for holding the implant in the body tissue once the implant is in place in the body. An expanded configuration may also or instead aid in bioabsorption of a bioabsorbable implant, such as by providing access of body fluids involved with bioabsorption to the implant. A range of configurations in between the delivery and deployed configurations may, for example, aid in guiding the implant to a desired location during deployment.

In some variations, an arm of an implant may be adapted to move relative to the implant body. An arm may be adapted to move away from, move around, or move towards a central axis of the implant body. An arm or a portion of an arm may include a material that is adapted to move the arm from a first position to a second position. A material to move the arm may, for example, be a resiliently deformable material or a shape memory material. An arm may be biased to move to a second position.

Two or more arms may be adapted such that they can be moved (e.g., pushed or pulled) towards or away from one another without breaking or cracking. An arm may be sufficiently movable (e.g., deformable, flexible, etc.) to travel up to 10°, up to 20°, up to 30°, up to 40°, up to 45°, up to 50°, up to 60°, up to 70°, up to 80°, up to 90°, up to 145° or up to 180° relative to a central longitudinal axis of the implant body from a first position to a second position without breaking or cracking, or may travel between any of the these ranges (e.g., travel from 30° up to 70°, from 10° up to 50°, etc.) In some examples, an arm in a first position on an implant may be oriented parallel (or close to parallel) to a central longitudinal axis of an implant and then may be moved to a second position so that the arm is obliquely oriented (e.g., as described above, up to 10°, up to 20°, etc.) with respect to its first position and the central axis of the implant body.

In some examples, the implant has first and second arms, and the distal ends of the arms are adapted to move away from a central longitudinal axis of the body. The first and second arms may move from a delivery configuration toward a deployed configuration, or from a contracted to an expanded configuration. In some examples, the first and second arms are biased towards their deployed configuration. In some examples, the biased arms may move from a delivery configuration toward a deployed configuration when a force from a delivery device is removed, such as by removing the implant from the device.

Arms on an implant, such as first and second arms 76*a* and 76*b*, may have different shapes or different configurations, or they may have the same shape or same configuration. The arms may be mirror images of each other. Instead of, or in addition to distal arms, a distal end may have protrusions. An arm or protrusion may be useful for carrying out an implant or implant arm function, and they may work alone, with one another, or with another structure in order to carry out the function(s). Such functions may include, for example, guiding the implant in a delivery tool, orienting the implant in a delivery tool, orienting the implant relative to an actuator (pushrod), a delivery tool, or patient tissue, holding the implant in a delivery tool, orienting the implant with respect to the patient, cutting or enabling arm travel through patient tissue, compressing or moving patient tissue, holding the implant in the patient tissue, placing a force on the patient tissue, and so on. An arm or protrusion may be or may have a barb, a bump, a cilia or cilia-like, a generally elongated rod, a hair, a hook, a loop, a prong, a rod, a spike, a thread, a tine, etc. An arm or protrusion may be relatively rigid or may be relatively flexible. An arm or protrusion may be more flexible or more rigid than another part or all of the rest of an implant. An arm or protrusion may place a force on another part of an implant, on another implant or on a body tissue. Am arm or protrusion may provide or cause friction (e.g., static friction) between an arm or protrusion and another part of an implant, on another implant or on a body tissue. An implant may have one or more than one arm, projection or protrusion such 2, 3, 4, 5, 6, more than 6, more than 10, more than 20, more than 100, more than 1000, etc. An arm or protrusion may be relatively flexible in a first dimension (e.g., in a depth or when extending away from a central longitudinal axis of the implant and relatively less flexible or inflexible in a second axis (e.g., along a width or from side to side or along a length). An arm may be configured to be able to be drawn or pushed inward (e.g., towards a central longitudinal axis of the implant) and to be pushed or extended outward (e.g., away from a central longitudinal axis of the implant).

Figure 3B:
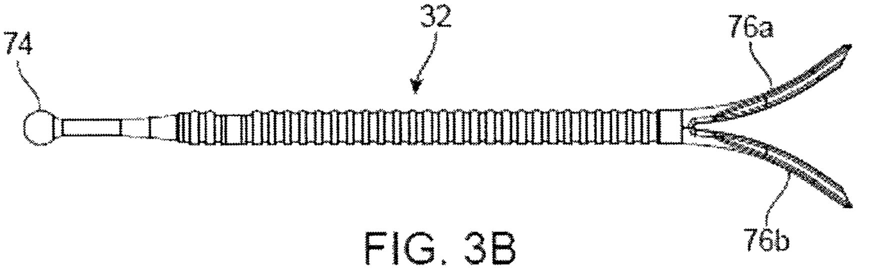
Figure 4B:
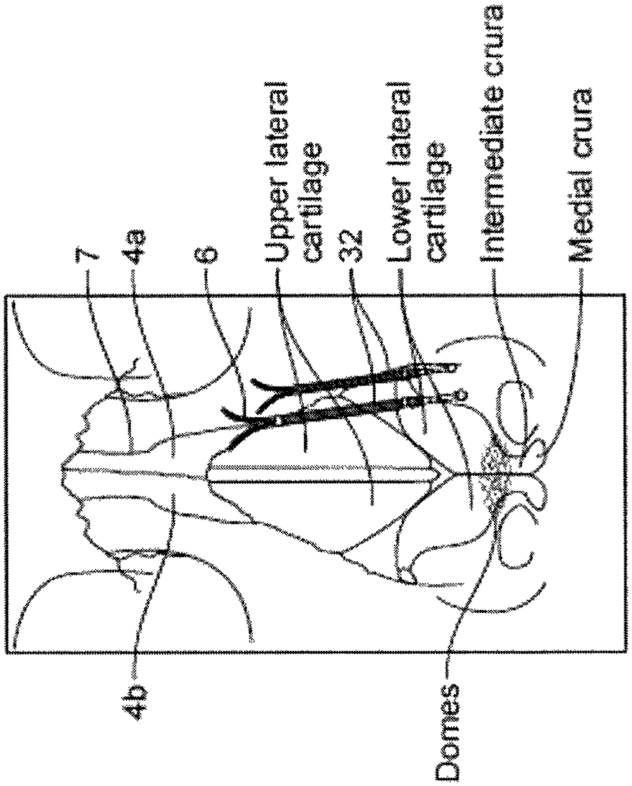
FIGS. 4A-4B show the placement of multiple implants in a patient's nose.
Figure 4A:
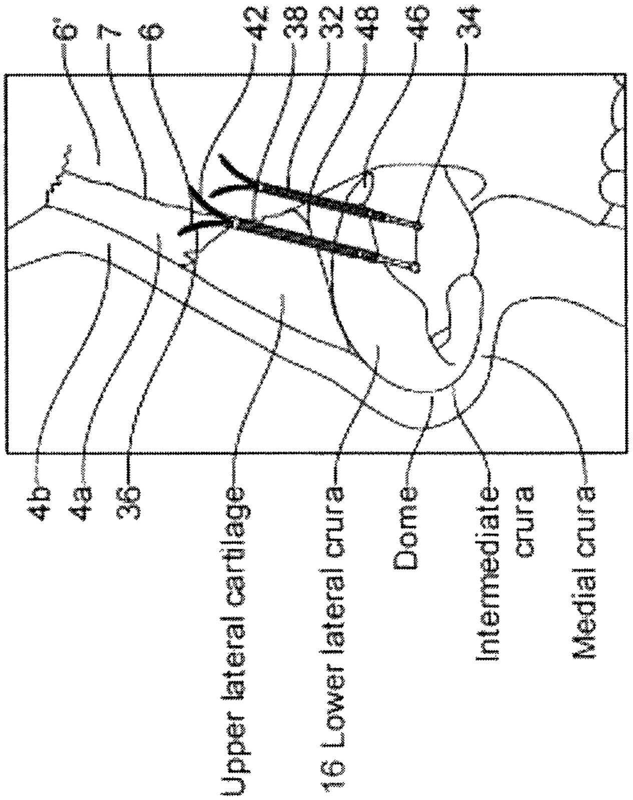

FIGS. 3A-3B also shows first arm 76*a* and second arm 76*b* having respectively, first arm inner bevel 80*a* and second arm inner bevel 80*b*, on radially inward surfaces of the distal end 72 of implant 32. A bevel (e.g., a slanted surface that meets another at any angle but 90°), especially an inner bevel, may be useful, for example, for guiding an implant or implant arm through body tissue. First arm inner bevel 80*a* has a first sharp edge 81*a* and second arm inner bevel 80*b* has a second sharp edge 81*b*. A sharp end of an inner bevel may be especially useful for cutting through tissue during implant deployment and to provide a path in body tissue for an implant arm to travel. For example, a sharp end of an inner bevel may cut or move through tissue without causing undue tearing or excessive damage. In some examples, an implant with a body and an arm, a cross-sectional area of the arm is smaller than is a cross-sectional area of the body. Generally, a small sharp cut through a tissue causes less pain and heals better than does a tissue that has been torn or subject to a larger cut. As described in more detail below, a sharp end of a bevel may cut through the tissue, and the angled end portion of the bevel and the rest of the arm may follow the sharp end as it moves through the tissue during implant deployment. The cut, slice or path through the tissue on the distal end may have a smaller cross-sectional area than does the implant body or the tissue contacting portion of an implant delivery device. Because the bevel acts to guide the arm through the tissue in front of a delivery device and the arm is smaller than the distal end of delivery device which houses the implant: the cut made by the bevel and the insertion path created by the bevel and arm may in some cases need only to be large enough for the arm to move through it; it does not need to be large enough for the delivery device or the implant body to move through. An implant with a flexible or otherwise movable arm (e.g., relative to an implant body) may be pushed or otherwise propelled through a body tissue during implant deployment, and the face (or angled portion) of an inner bevel may push against body tissue, urging the arm away from the central longitudinal axis of the implant body (and towards a deployed configuration). Instead, or additionally, an implant arm may be biased towards a deployed configuration, and the bevel may help move the biased implant arm towards a deployed configuration and deployed implant position in body tissue.

FIG. 3A also shows first arm 76*a* or second arm 76*b* each having respectively, first arm outer bevel 78*a* and second arm outer bevel 78*b*, on radially outward surfaces of distal end 72 on implant 32. An outer bevel may be useful, for example, for guiding an implant into a delivery device, for contracting an implant into a contracted configuration, for orienting an implant in a delivery device, for guiding an implant through a delivery device, etc. Inner bevel 80*a* and outer bevel 78*a* on first arm 76*a* form a double bevel: the bevels or slanted surfaces share an edge (e.g., the two slanted surfaces meet each other at any angle but 90°) or may flare away from each other. In some examples, first and second or inner and outer bevels or slanted surfaces that meet another at any angle but 90° and do not share an edge (e.g., the bevels form from different edges). An implant or an arm or a protrusion may have one or more than one bevel or sloped surface or edge that meets another at any angle but 90°. A bevel may be at an end of an arm or protrusion or along a side of a projection or protrusion.

Figure 23A:
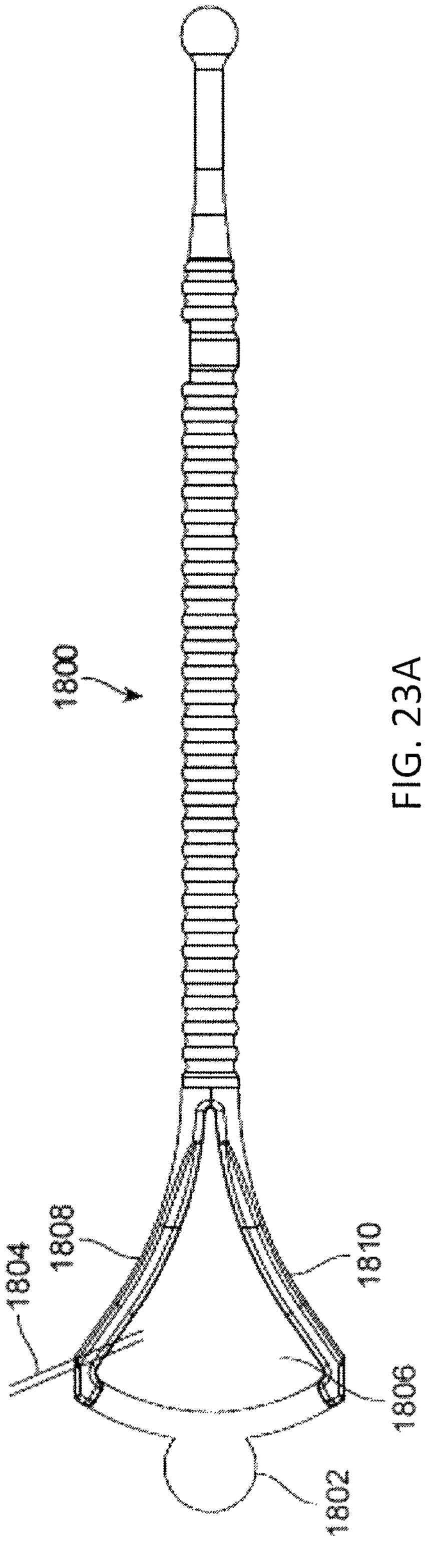
FIGS. 23A-23B show drawings of an implant.
Figure 23B:
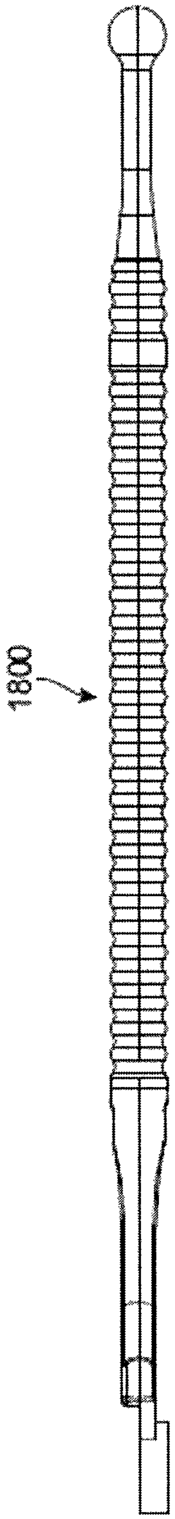

FIGS. 23A-23B show drawings of a molded implant 1800 with beveled ends having a holding element 1802 for use in manufacturing. After forming the device, cuts may be made along lines 1804 and 1806 to create beveled ends of the arms 1808 and 1810, respectively, such as the 63 degree trim angle shown.

Figure 24A:
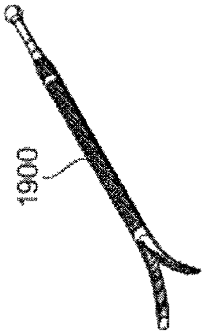
FIGS. 24A-24F show drawings of an implant.
Figure 24B:
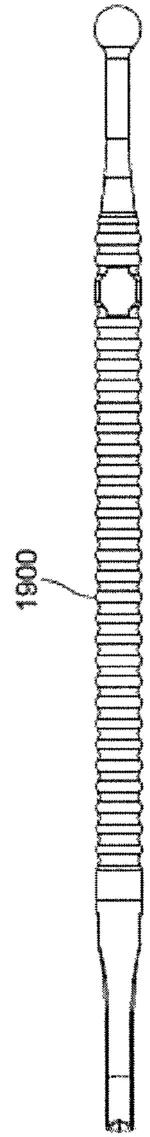
Figure 24C:
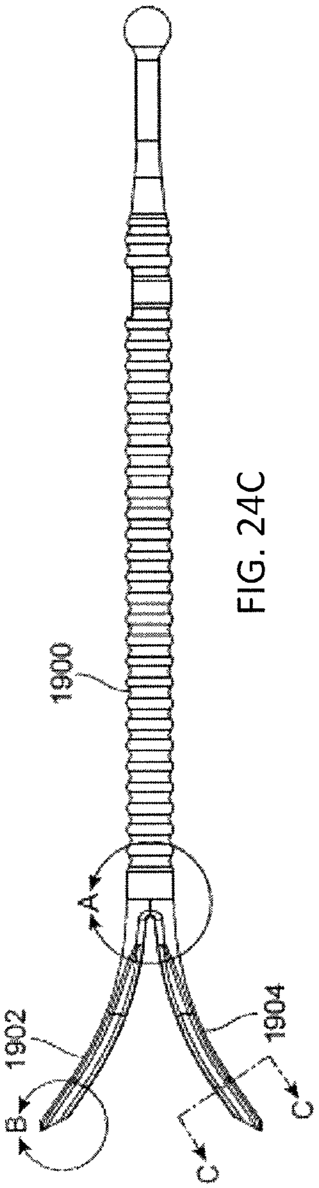
Figure 24D:
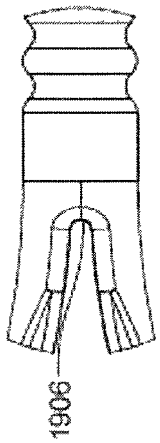
Figure 24E:
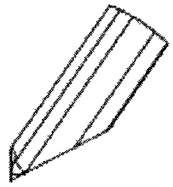
Figure 24F:
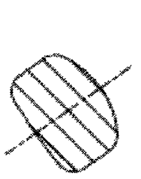

FIGS. 24A-24C show drawings of a molded implant with beveled ends. As shown, the overall length of the device 1900 may range from 0.74 inches to 1.04 inches. Arms 1902 and 1904 have an at-rest spread at their tips of 0.166 inches to 0.206 inches. These drawings exemplify dimensions that may be employed for the implants of this invention, as discussed in more detail above. Detail A of FIG. 24C illustrates the intersection of arms 1902 and 1904 at point 1906. The intersection of arms 1902 and 1904 at point 1906 forms an angle. The angle illustrated in FIG. 24C is an acute angle less than 90°. In some embodiments the arms 1902 and 1904 can engage with tissue such that the arms 1902, 1904 form an angle that is less than 90°. In some embodiments the angle between the arms 1902, 1904 is less than 180° when the implant is implanted in the tissue.

Figure 25:
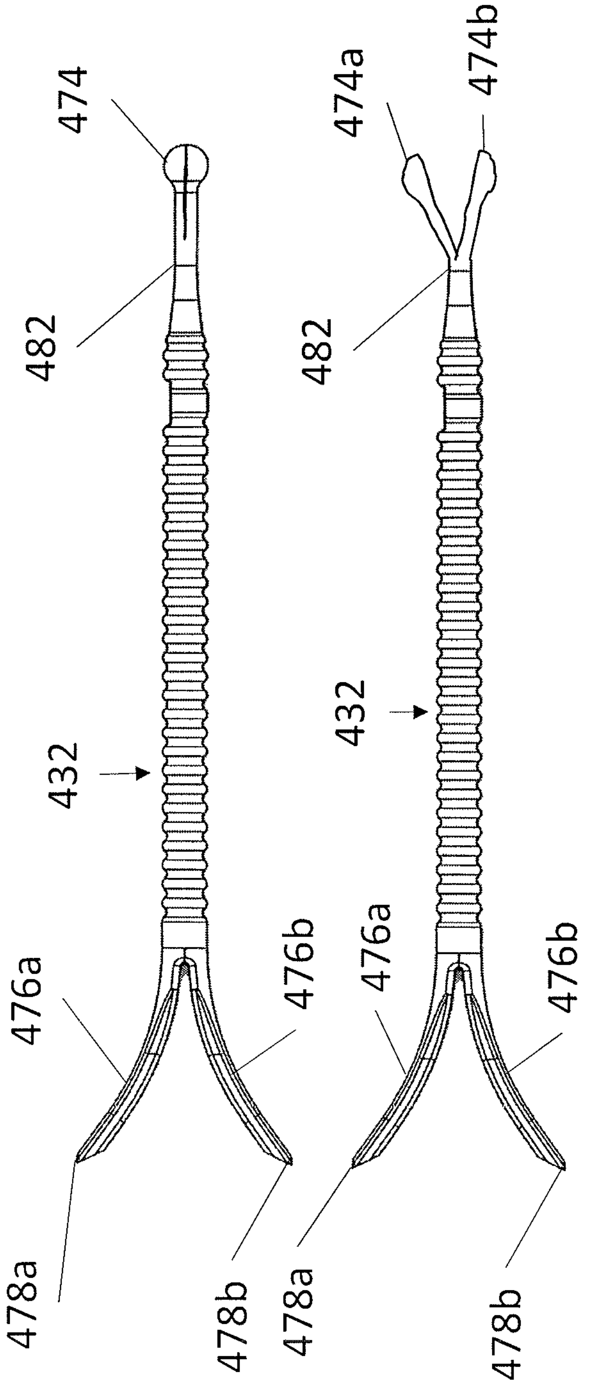
FIG. 25 shows an implant in accordance with some embodiments.

The implants can also include one or more barbs, forked features, or expanding features on the proximal end of the implant. The forks, barbs, or expanding features at the proximal end of the implant can prevent the implant from migrating back out of the insertion point. FIG. 25 illustrates an implant 432 with a proximal tip that can open up after exiting the needle to prevent migration of the implant after deployment and withdrawal of the delivery tool/needle. The implant 432 has a proximal feature 474 at the proximal end. As shown the proximal feature 474 is a blunt end The implant 432 has a second (or distal) end with a first arm 476*a* and a second arm 476*b*, each arm having a proximal end fixed to the body and a distal end not fixed to the body. The first arm 476*a* and second arm 476*b* can each have respectively, one or more outer bevels 478*a* and outer bevel 478*b*, on radially outward surfaces of distal end of implant. The outer bevels 478*a*, 478*b* can enable each arm 476*a*, 476*b*, respectively, to engage with surrounding tissue. Implant 432 also has strain relief section 482. As shown, strain relief section 482 has a relatively smaller cross-sectional area (e.g., a diameter) than another portion of the implant. The implant 432 shows the proximal feature 474 in a compressed or non-expanded configuration and an expanded configuration. In the expanded configuration the proximal feature expands with barbs/arms 474*a*, 474*b*. The barbs, forked features, or expanding features of the proximal end can be smaller than the distal end arms (476*a*, 476*b*) because they are sized to prevent the implant from migrating or moving with respect to the tissue surrounding and adjacent to the proximal end of the implant.

The implants disclosed herein can include multiple materials to tailor the stiffness of the implant, outer hardness/softness, biocompatibility, and absorption profile of the implant. In some embodiments the implants can include an inner structure that is degradable with an outer coating that is hydrophobic. The degradable material can degrade in vivo through hydrolysis. Degradation can be slowed by coating the degradable material with a coating, such as a hydrophobic coating to control or tune the degradation of the implant. The hydrophobic coating can delay ingress of water and subsequently delay hydrolysis of the degradable portion of the implant. An example of a hydrophobic material that can be used is polycaprolactone, which is an absorbable material that is hydrophobic, crystalline, and highly elastic making it well suited for a coating. The coating could be applied with a specifically selected blend of solvents to minimize the impact on the underlying polymer structure. In some embodiments a non-absorbable biocompatible coating, such as a silicone, an epoxy acrylate, or Parylene™ could be used to slow the absorption of water into the underlying polymer.

The biodegradation rate, profile, and/or period of the implant can be tuned. For example, a multitude of coatings both absorbable and non-absorbable can be applied to an underlying implant structure that already exhibits the necessary mechanical properties for supporting upper and lower lateral nasal cartilage. Many possible coatings exist including polycaprolactone, silicone, fluoropolymers, vinyl alcohol, acrylates, etc. In some embodiments the coating can be Parylene™. An exemplary hydrophobic coating compound, Parylene™ (poly(dichloro-para-xylylene)) has the forms:

Parylene N

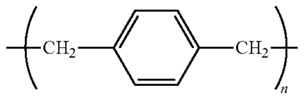

Parylene C

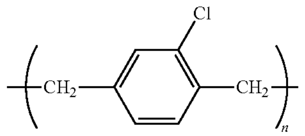

-continued

Parylene D

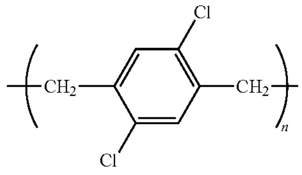

Parylene™ N is the basic member of the family and is typically most permeable to moisture. Parylene™ C and D are typically used for moisture barrier properties. Existing forms of Parylene™ have been primarily used as a complete moisture barrier for electronics and medical implants due to typically pinhole free coating properties. In some cases Parylene™ can be used as a control release agent for drugs being released out of a material below the coating. For example, the drug can be in a layer or material beneath the Parylene™ coating. In other forms of coatings, Parylene™ can also be used for adding lubricious coatings on guidewires and catheters. In the present disclosure Parylene™ is used differently than the traditional applications. In one embodiment the semi-permeable nature of extremely thin coating layers can be used advantageously to control water ingress through the thin coating and into contact with the underlying implant structure. The biodegradation rate of the implant can be controlled by selecting and controlling the thicknesses and conformality of the coating, such as a Parylene™ coating.

The conformal coating process for Parylene™ is well established and allows for controlling the thickness of the coat on the implant substrate. In order to facilitate some water transmission through the Parylene™ coating and initiate hydrolytic degradation, the implant may be coated at thicknesses in the range of about 0.1 to about 10 microns, preferably in the range of 0.1 to 5 micron to allow for a semi-permeable design. The design of a semi-permeable coat achieves selective tuning of the absorption rate of the implant, where the extent of permeation is determined by the coating thickness and conformality.

The thickness of the hydrophobic coating can be selected to modify the absorption profile of the implant. In some embodiments the thickness of the hydrophobic coating can be from about 0.1 micron to about 10 microns. In some embodiments the thickness of the hydrophobic coating can be from about 0.1 micron to about 5 microns. In some embodiments the thickness of the hydrophobic coating can be from about 0.1 micron to about 1 micron. In some embodiments the hydrophobic coating has a thickness of less than 10 microns. In some embodiments the hydrophobic coating has a thickness of less than 5 microns. In some embodiments the hydrophobic coating has a thickness of less than 1 micron. The thickness of the coating can be selected to control the rate of water ingress through the coating and into the core of the implant.

The hydrophobic coating can be applied to the entire outer surface of the implant or portions of the outer surface of the implant. In some embodiments the hydrophobic coating is applied to a central rod portion of the implant. In another embodiment the hydrophobic coating is applied to the implant except for the ends. For example, the proximal end or tip can be uncoated to act as a site for water ingress.

The conformality of the hydrophobic coating can also be selected to modify the absorption profile of the implant. In some embodiments the conformality of the hydrophobic coating is selected to control the rate of water ingress through the hydrophobic coating and into the core of the implant. In some embodiments the hydrophobic coating has a patterned conformality with coated sections and open sections. The patterned hydrophobic coating can be applied over the entire outer surface of the implant or on portions of the implant. In some embodiments the hydrophobic coating can have a porous structure.

In some embodiments the hydrophobic coating can have a laminated structure made out of multiple materials. For example, a combination of bioabsorbable layers and non-bioabsorbable layers can be used in some embodiments to tune the degradation rate or profile of the implant after implantation in the nasal tissue.

The coatings can be applied using a variety of processes, such as vapor deposition, dip coating, spray coating, sputter coating, brush layering, etc.

In some embodiments the hydrophobic coating is bioabsorbable. In the case of polycaprolactone, the coating itself is hydrophobic and bioabsorbable allowing for complete resorption over time. Using a dip coating method, a coating thickness of 0.1 to 10 microns can be achieved for desired results. Additionally, the same effect can be achieved by depositing 0.001 to 20 weight percent of polycaprolactone on the implant substrate. Polycaprolactone is dissolved readily in a mixture of various solvents consisting of but not limited to cycloalkanes, organic esters, chloroform and other such organic solvents.

The degradation profile rate can be selectively tuned such that the life of the implant core or implant base polymeric substrate can be increased up to 20-fold.

Figure 26:
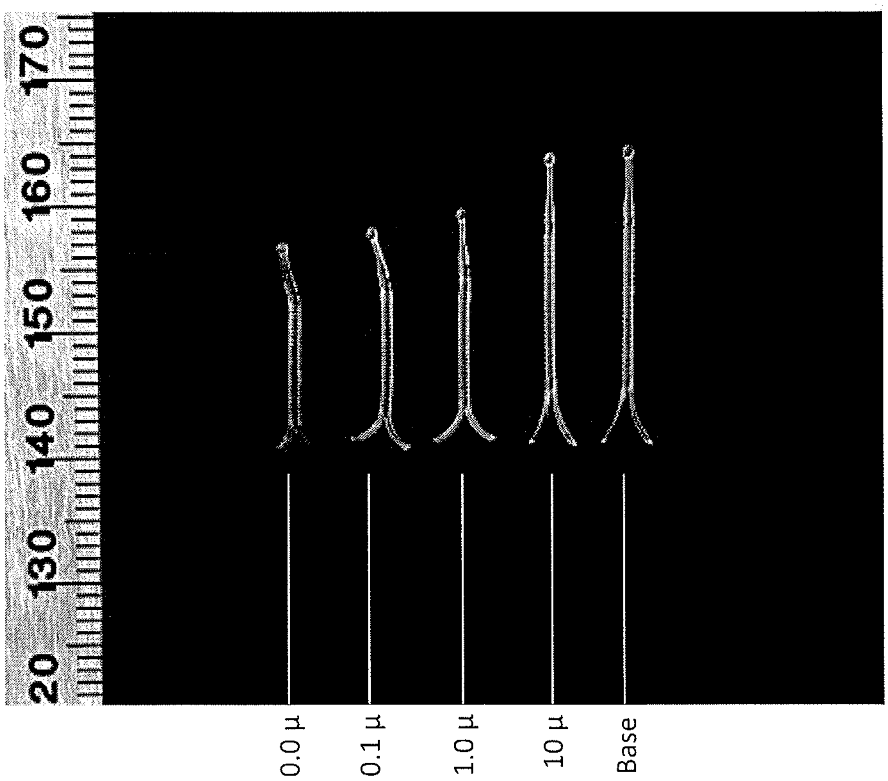
FIG. 26 illustrates examples of implant cores having varying coating thicknesses in accordance with some embodiments.

FIG. 26 illustrates examples of implant cores having varying coating thicknesses. The base shows the implant core prior to exposure to accelerated physiological conditions as a control comparison to the other implant configurations shown in FIG. 26. The accelerated physiological conditions included high temperature saline conditioning to accelerate the impact of moisture penetration. The accelerated physiological conditions can simulate extended exposure to physiological conditions. The implant cores have coatings of 0.0μ, 0.1μ, 1.0μ, and 10μ. FIG. 26 shows that the thicker the coating the lower the amount of degradation of the implant for the exposure of the illustrated implants to accelerated physiological conditions. The core with no coating degraded the most while the 10μ coating degraded the least. The coating thickness, conformality, and patterning can be selected to tune the degradation of the implant in physiological conditions.

Figure 27A:
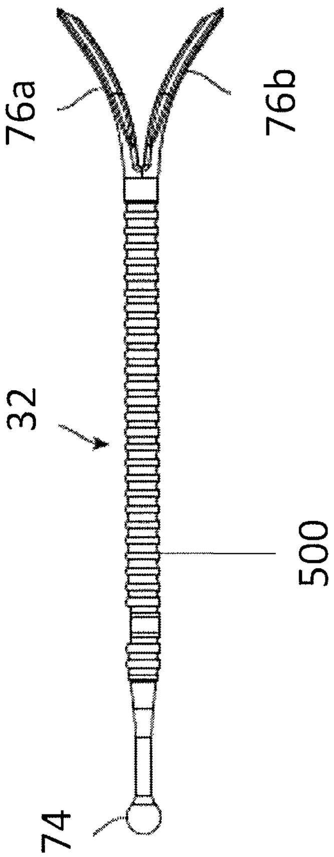
FIGS. 27A-27D illustrate embodiments of nasal implants with various coating configurations.
Figure 27B:
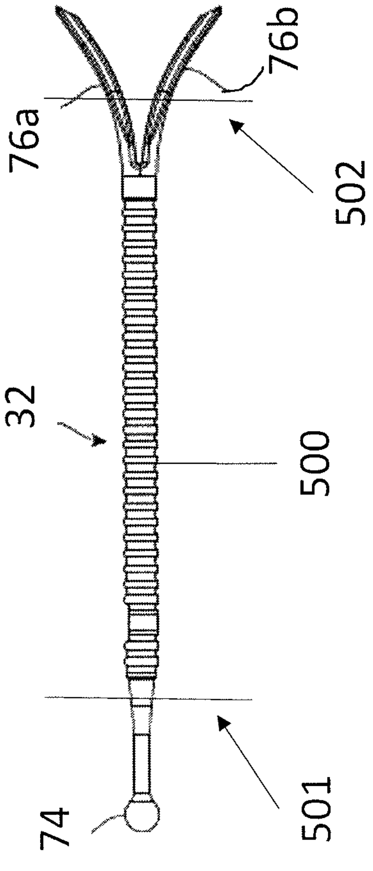
Figure 27C:
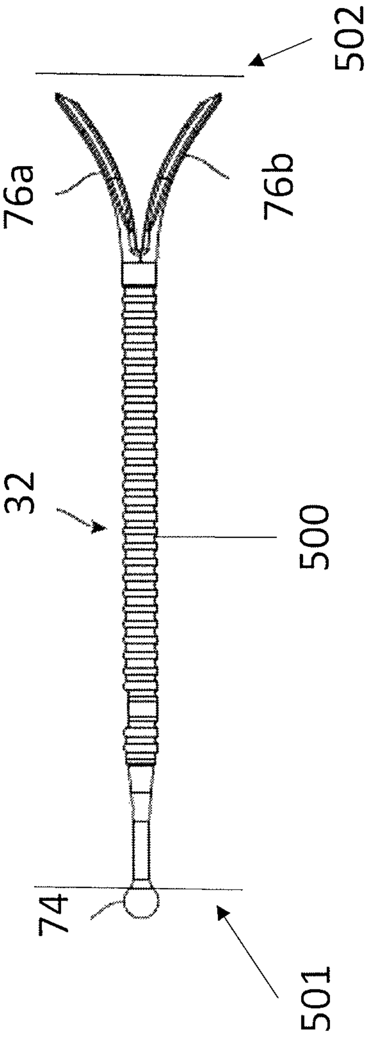
Figure 27D:
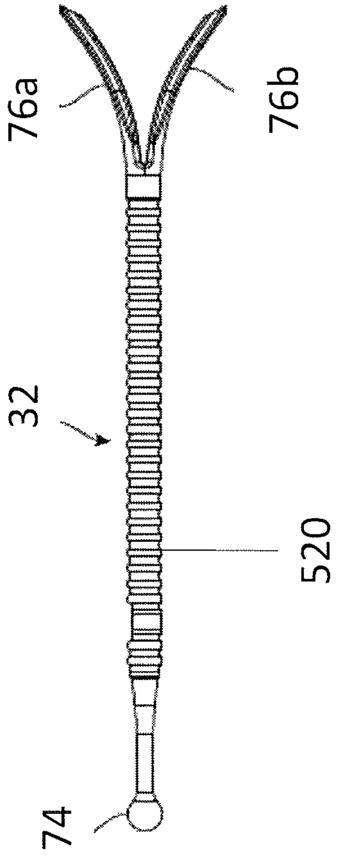

FIGS. 27A-27D illustrate embodiments of nasal implants with various coating configurations. FIG. 27A shows the implant 32 with a coating 500 over or on substantially the entire outer surface of the implant 32. The coating 500 can slow down or prevent water ingress to slow down the degradation of the implant 32 after implantation in the tissue. FIG. 27B shows the implant 32 with a coating 500 over a central longitudinal portion of the implant between lines 501 and 502. The absence of the coating 500 over the proximal end and the distal end allows water ingress to the implant 32 through the uncoated sections to promote degradation of the implant 32. FIG. 27C shows the implant 32 with a coating 500 over the outer surface of the implant including the central longitudinal portion of the implant 32 and the arms 76*a*, 76*b* of the implant. The proximal feature 74 is not covered by the coating 500 to allow water ingress into the implant to promote degradation of the implant 32 through the proximal feature 74. FIG. 27D shows the implant 32 with a discontinuous coating 520 over or on substantially the entire outer surface of the implant 32. The discontinuous coating 520 can slow down or prevent water ingress over the coated portions to slow down the degradation of the implant 32 after implantation in the tissue while allowing water ingress through the discontinuous portions to promote degradation of the implant 32 at the uncoated portions.

An implant, arm, or protrusion may have other or additional features such as a gripper, a prong, a tooth, etc. A feature may be angled relative to the implant, arm, or protrusion such that the feature holds the implant, arm, or protrusion in place in a delivery device or tissue. A feature on an arm or protrusion may limit or prevent substantial proximal and/or distal implant movement or side-to-side (lateral) movement. FIG. 3A shows implant 32 with a plurality of segments.

An implant may have one or more proximal end features, distal end features, or body features such as described herein or any features shown in US 2011/0251634 to Gonzales et al., US 2012/0109298 to Iyad Saidi; or U.S. patent application Ser. No. 14/192,365 filed Feb. 27, 2014. FIGS. 3A-3B shows implant 32 with proximal feature 74 at the proximal end. As shown, proximal feature 74 is a blunt end. A proximal feature may be sharp or flat, but in general will be rounded or atraumatic. An atraumatic end may prevent the proximal implant end from damaging, cutting, or exiting a tissue when it is in place in the tissue, such as in a nasal tissue. A proximal feature may help to anchor or otherwise hold an implant in place in the tissue in which it is implanted. As described in further detail below, a proximal feature may also be configured to accept or mate with a plunger or actuator to aid in orienting the implant in a delivery device or in moving the implant through a delivery device and implanting the implant into tissue. A proximal feature and an actuator or plunger may interact in any way that allows the actuator to move the implant. For example, an implant may have concave end and a plunger or actuator may have a convex end. Implant 32 also has strain relief section 82. As shown, strain relief section 82 has a relatively smaller cross-sectional area (e.g., a diameter) than another portion of the implant. A strain relief section may be larger than another area, but may provide strain relief by having a different configuration or a different material. A strain relief section may be more flexible or may have a less flexural rigidity than another region of the implant. A strain relief region may be useful to accommodate movement of a tissue, such as a nose so that the nose can bend. An implant for use in nasal or facial tissue may be configured so that the strain relief section is adjacent to mucosa to accommodate movement of the nose when the implant is in place in a nasal tissue. A strain relief section may work in conjunction with a proximal feature such as a blunt end to hold an implant in a tissue (e.g., tissue may form a collar around the neck and the proximal end may prevent movement through the collar).

Implant 32 also has a central bridging region. The central bridging region may be especially useful for bridging an area in need of support, such as weak or collapsed area between structures on either (both) ends. Such an area may be weaker or may have more force generally placed on it such that it requires more support. A central bridging region may bridge a weak or collapsed nasal valve in a nose. Support for the bridging region may be provided from the regions of the implant near the bridging region. A central region may include one or more ribs (also called ridges). Implant 32 has a plurality of ribs 80*a*, 80*b* (or ridges) which may be a central bridging region. Body features such as a rib may help anchor an implant in place, such as by catching tissue against the rib, valley, or otherwise. An implant may have one or more ribs or other body features, such as a bevel, scallop, a wing, etc. An implant may have from 0-50 body features (such as ribs), or no body features (such as ribs), 1 body features (such as ribs), 2 body features (such as ribs), 3 body features (such as ribs), 4 body features (such as ribs), 5 body features (such as ribs), from 5 body features (such as ribs) to 10 body features (such as ribs), from 10 body features (such as ribs) to 20 body features (such as ribs), from 20 body features (such as ribs) to 30 body features (such as ribs), from 30 body features (such as ribs) to 50 body features (such as ribs), etc. or any amount of body features (such as ribs) in between any of these numbers. As shown in FIG. 3A a first rib has a first rib width W1 and a second rib has a second rib width W2. Rib widths W1 and W2 may be the same size or may be different sizes. A first rib may have a first rib diameter and a second rib may have a second rib diameter. The first and second rib diameters may be the same size or may be different sizes. For example, ribs along one end, such as the distal end, may be thicker or have a large diameter to provide more leverage (e.g., against a maxilla bone), while ribs along the proximal end may be thinner or have a smaller diameter to allow more implant flexibility. In other cases, a feature along the distal end may be thinner or have a smaller diameter, for example to reduce or eliminate any undesired rib profile that may be visible on the outside surface of the nose. A feature such as a rib may be thinner and allow movement of the nose, such as during breathing (inspiration and expiration). A rib may provide a relatively larger implant surface area which may aid in speed or uniformity of biodegradation of a biodegradable implant. Ribs may aid in the flexibility of the implant; having more ribs or having larger valleys between the ribs may increase the implant flexibility.

In some variations, an implant may have a relatively low profile (e.g., short height) in at least one dimension (length, width, height). An implant height may, for example, less than 1 mm, less than 2 mm, less than 3 mm, less than 4 mm, less than 5 mm, less than 10 mm, less than 20 mm, or any size in between these, e.g., from 1 mm to 2 mm, from 1 to 5 mm, from 2 mm to 4 mm, etc. A low profile implant may be particularly beneficial, for example, because it may be inserted through a relatively small implant hole that heals easily, it may be the desired shape to fit anatomy of the space into which it is implanted, or it may not be obviously visible when implanted. An implant height may be chosen based on the implant environment and desired effect of the implant. For example, in the face and nose, underlying cartilage and bone generally determine face and nose shape, though muscle and skin play a role as well. The muscle, skin and associated tissues that cover the underlying cartilage and bone tend to take on the shape of the underlying structure that they cover. Skin and muscle thickness vary between individuals. Some people have relatively thicker skin and muscle and others have thinner skin and muscle. A relatively tall implant located over cartilage or bone may cause an obvious bump or protrusion in overlying thin muscle and skin that may be noticeable simply by looking at the person who may feel uncomfortable or self-conscious due to the attention, but may not cause an obvious bump or protrusion in a person with thicker muscle and skin which may better accommodate or mask the implant. An implant with a relatively small height may create a relatively low profile that is not obvious through the skin when the implant is in place in the nose. A low profile implant may in some cases make a small bump or protrusion that is detectable by close inspection or palpation. A body of implant may be curved or bent (and may have various features that are not straight), but in general will be relatively straight and able to bend or flex. For example, an implant may flex to a minimum bend radius of 15 mm+/−0.5 mm.

Different regions of an implant may have material properties, such as strength, flexibility, rigidity, flexural rigidity, etc. An implant may have a material property chosen to come close to a material property of a body structure. For example, a flexural rigidity of a nasal implant may be the same as or close to the flexural rigidity of nasal tissue such as cartilage. As described below, some nasal cartilage has a modulus of elasticity measured to be between 5 and 32 MPa. An implant, or a portion of an implant such as a central region, an end region, an arm region, a proximal feature, a distal feature, a protrusion, a bump, or other part of an implant as described herein may have a modulus of elasticity between 5 and 32 MPa or greater than 2, 4, 5, 10, 15, 20, 25, 30, 32, 35, 40, or 50 MPa or less than 2, 4, 5, 10, 15, 20, 25, 30, 32, 35, 40, or 50 MPa or any value in between, such as between 2 and 50 MPa, between 10 and 30 MPa, etc. A flexural rigidity of some batten grafts formed of septal cartilage has been determined to be between 50 and 130 N-mm2 or 50-140 N-mm2 and the flexural rigidity of an implant or portion of an implant may also be within this range. An implant flexural rigidity may also be greater or less than this. For example, other supporting structures in a body may work with an implant in providing additional support and a lesser amount of support is needed from the implant or supporting tissues may also be weak and greater support may be needed from the implant. An implant, or a portion of an implant such as a central region, an end region, an arm region, a proximal feature, a distal feature, a protrusion, a bump, or other part of an implant as described herein may have a flexural rigidity of greater than 10, greater than 30, greater than 50, greater than 75, greater than 100, greater than 150, greater than 200, greater than 300, greater than 400 or less than 600, less than 500, less than 420 less than 400, less than 300, less than 200, less than 130, less than 100, less than 50. For example, an implant or portion of an implant may have a flexural rigidity between 10 to 590 N-mm$^2$; of 30 to 450 N-mm$^2$; of 60-250 N-mm$^2$; of 75-200 N-mm$^2$; 50 and 130 N-mm$^2$; or 9 and 130 N-mm$^2$. In some embodiments the implant has a central portion with a flexural rigidity that is less than about 130 N-mm$^2$. In some embodiments the implant has a central portion with a flexural rigidity that is from about 10 to about 130 N-mm$^2$. In some embodiments the implant has a central portion with a flexural rigidity that is about 50 to 130 N-mm$^2$. The material properties of a bioabsorbable implant change over time; thus a bioabsorbable implant be configured to have any of the material properties, such as those described above after a period of time in a body or exposure to a body fluid.

An implant may be made of any biocompatible material that provides the desired support and shaping properties of the implant. An implant may be partially or wholly made from a non-biodegradable material as known in the art such as any polymer, metal, or shape memory material. An implant may be made from organic and/or inorganic materials. A material of the implant may be solid, (e.g. titanium, nitinol, or Gore-tex), braided or woven from a single material (such as titanium, or Polyethylene Terephthalate, or a combination of materials). A woven material may have pores which allow ingrowth of tissue after implantation. Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyacrylamides, polyorthoesters, polypheazenes, polysiloxanes, polyurethanes, polyvinyl alcohols, polyvinyl esters, polyvinyl ethers, polyvinyl halides, polyvinylpyrrolidone, poly(ether ketone)s, silicone-based polymers and blends and copolymers of the above.

Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane, poly(lactic acid), poly(butyric acid), poly(valeric acid), poly[lactide-co-glycolide], poly(fumaric acid), poly(maleic acid), copolymers of poly (caprolactone) or poly(lactic acid) with polyethylene glycol and blends thereof.

A polymer used in implants may be non-biodegradable. Examples of non-biodegradable polymers that may be used include ethylene vinyl acetate (EVA), poly(meth)acrylic acid, polyamides, silicone-based polymers and copolymers and mixtures thereof.

In some embodiments the implant can include one or more bioabsorbable materials in combination with a non-absorbing material. For example, in some cases at least one of the distal end, proximal end, or central portion is composed of a core made of a non-absorbable or an absorbable material. The implant can then include an outer layer made of a different non-absorbable or absorbable material from the core. In some examples the core and outer layer are fixedly laminated to one another. In other examples the core and outer layer are slid-ably engaged with one another.

In some embodiments the first and second arms of the implant are configured to self-expand toward the deployed configuration. In some embodiments the first and second arms of the implant are configured to move to the deployed configuration through engagement with tissue or part of the delivery tool.

For example, an implant or arms or features on an implant may include shape memory material. In some variations, an implant includes a biocompatible, bioabsorbable material such as a bioabsorbable polymer. A bioabsorbable or biodegradable implant may provide structure and support to a body tissue, such as nasal tissue, for a temporary period of time and may induce or cause the formation of scar or other tissue that provides structure and support to the body tissue for a longer period of time, including after the implant is degraded. Biologically formed scar or other tissue may be beneficial because it may be more comfortable, provide longer term support, stay in place better, etc. than does an implant. Part or all of an implant may be degradable in vivo (also referred to as biodegradable) into small parts and may be bioabsorbable. An implant or implant body may consist essentially of a bioabsorbable material. An implant or implant body may include two or more than two different bioabsorbable materials. A method as described herein may include biodegrading and bioabsorbing an implant or just part of an implant if an implant includes both bioabsorbable and non-bioabsorbable parts. Bioabsorbing may be facilitated by tissues and organs. Tissues and organs that bioabsorb may include bodily fluids, such as blood, lymph, mucus, saliva, etc. Bacteria may also aid in bioabsorbing a material. An implant may be partially or wholly made from one or more biocompatible biodegradable material, such as from a naturally occurring or synthetic polymer. A biodegradable implant may be made from a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly (lactide-co-glycolide)/poly(ethylene glycol) copolymers; a poly(lactic acid)/poly(ethylene glycol) copolymers; a poly (glycolic acid)/poly(ethylene glycol) copolymers; a poly (lactic acid-co-glycolic acid)/poly(ethylene glycol) copolymers; a poly(caprolactone); poly(caprolactone)/poly (ethylene glycol) copolymers a poly(orthoester); a poly (phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly (oxyethylene)/poly(oxypropylene) copolymer, or a blend or copolymer thereof. In some examples, an implant includes poly-L-lactic acid (PLLA) or poly-D-lactic acid (PDLA) or both. In some examples, an implant is 90:10, 80:20, 70:30, 60:40, 50:50 PLLA/PDLA copolymer or is in between any of these values. In some examples, an implant is 70:30, +/−10% PLLA/PDLA copolymer.

The implant can have different sections made out of different bioabsorbable materials based on the desired characteristics for each section and based on the type of tissue that each section engages with and the typical properties of the type of tissue. It can be desirable for the arms and central section of the implant to provide structural support longer than the proximal end. For example the arms and central portion can be made of a first bioabsorbable material having a first bioabsorption profile and the proximal end can be made of a second bioabsorbable material having a second bioabsorption profile. The second bioabsorption profile can be shorter than the first bioabsorption profile.

A biodegradable implant or portion of an implant as described herein may be configured or tuned to biodegrade (to be absorbed) in less than 60 months, 36 months, less than 24 months, less than 18 months, less than 12 months, less than 9 months, less than 6 months, less than 3 months, or less than 1 month, or any time in between any of these times. For example, an implant may be configured to degrade from between 9 months and 12 months, between 3 months and 12 months, between 1 month and 12 months, etc. If an implant is entirely made up of biodegradable material, then the entire implant may degrade or mostly degrade in these times. For example, a biodegradable implant may degrade so that is has significantly altered material properties. The material properties of a bioabsorbable implant change over time; thus a bioabsorbable implant may be configured to have any of the material properties, such as those described elsewhere herein after any of the above periods of time in a body or exposure to a body fluid. In some examples, a bioabsorbable implant has (or is configured to have) a flexural rigidity of less than 15 N-mm2, less than 10 N-mm2, less than 5 N-mm2, less than 4.2 N-mm2, less than 4 N-mm2, less than 3 N-mm2, less than 2 N-mm2, or less than 1 N-mm2 after 3, 6, 9, or 12 months in a body. If an implant includes both biodegradable and non-biodegradable material, then the biodegradable portion may degrade in any of these time periods and the non-biodegradable material may not degrade. An implanted implant in a body may be exposed to body tissues and body fluids to cause biodegradation. An implant may be chosen or configured to biodegrade within the listed times for various reasons. For example, an implant with the desired material properties (e.g., flexibility, strength, etc.) that is exposed to mucous may degrade within a different time frame than an implant that is not exposed to mucus. An implant that degrades more slowly may allow more time for desired scar or other tissue to form before it degrades.

An implant may include additional materials, such as an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a steroid, a vitamin, etc. Such materials may be attached to, adhered to, coated onto, or incorporated into to an implant. Such materials may be inserted into a body tissue along with the implant. Such materials may be required at different times and may be time sensitive or time release. For example, an anti-inflammatory agent may be useful immediately after implantation to prevent too much early inflammation and pain, but may not be desirable during later stages of scar formation and healing as it may interfere with a healing process that provides new tissue to provide support for tissues once the implant is remove. For example, an implant may be configured to release a cartilage growth inducer, such as a fibroblast growth factor (FGF; such as basic fibroblast growth factor or FGF2) or a transforming growth factor (TGF; such as TGFβ1) after several days or weeks so as to prevent an inappropriate or unwanted response early on.

Additionally, these coatings can also be configured to elute thrombolytics, vasodilators, corticosteroids, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, free radical scavengers, antioxidants, biologic agents, radiotherapeutic agents, radiopaque agents and radiolabelled agents, such that the posited coating serves as a controlled release agent for the biopharmaceutical or the bioactive agents coated on the (implant) bioabsorbable substrate layer.

In certain embodiments a coating might be used to act as a tie layer between the substrate base implant material and the drug coating or even the coating being used to extend the degradation period.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A nasal implant delivery tool comprising:

a handle including an implant loading chamber adapted to receive a nasal implant;

a needle extending distally from the handle to a distal end, wherein the needle comprises a needle lumen having an opening at the distal end, wherein the distal end is sharp;

an actuator configured to move the nasal implant along the needle lumen and toward the opening at the distal end of the needle, wherein at least one of the implant loading chamber or the needle comprises a non-circular cross-section that is configured to control an orientation of the nasal implant such that the nasal implant is automatically in a predetermined orientation relative to the handle when the nasal implant is at the opening of the needle lumen; and an implant orientation indicator, wherein the implant orientation indicator is configured to provide a visual indication of a plane formed by a first implant arm and a second implant arm of the nasal implant corresponding to the predetermined orientation of the nasal implant in the needle, wherein the implant orientation indicator includes a first indicator arm projecting from the handle in a first direction and a second indicator arm projecting from the handle in a second direction, wherein the first direction is opposite the second direction, and wherein the first indicator arm is directly opposite of the second indicator arm on the handle, wherein the implant loading chamber comprises a recess that is configured to allow the nasal implant to be inserted into the implant loading chamber through a lateral portion of the handle.

2. The nasal implant delivery tool of claim 1, wherein the first implant arm and the second implant arm have (i) a contracted configuration in which the first implant arm and the second implant arm are contracted toward a central longitudinal axis of the nasal implant and (ii) an expanded configuration in which the first implant arm and the second implant arm extend away from the central longitudinal axis by a greater extent than when the first implant arm and the second implant arm are in the contracted configuration, and wherein the first indicator arm and the second indicator arm define a plane that is substantially parallel to the plane formed by the first implant arm and the second implant arm of the nasal implant when the nasal implant is in the predetermined orientation in the needle.

3. The nasal implant delivery tool of claim 2, wherein the first implant arm and the second implant arm each have an arc shape when the nasal implant is in the expanded configuration, and wherein the first indicator arm and the second indicator arm each have the arc shape.

4. The nasal implant delivery tool of claim 2, wherein the implant loading chamber is configured to receive the nasal implant while the nasal implant is in the expanded configuration.

5. The nasal implant delivery tool of claim 4, wherein the actuator is configured to move the nasal implant from the implant loading chamber to the needle lumen, wherein the implant loading chamber of the nasal implant delivery tool is configured to transition the nasal implant from the expanded configuration to the contracted configuration as the nasal implant moves through the implant loading chamber and into the needle lumen.

6. The nasal implant delivery tool of claim 5, wherein the first implant arm and the second implant arm are biased toward the expanded configuration, and wherein, while the nasal implant is in the contracted configuration in the needle lumen, the implant orientation indicator is configured to indicate the orientation that the nasal implant will be in when the nasal implant is delivered out the distal end of the needle lumen and transitions back to the expanded configuration.

7. The nasal implant delivery tool of claim 1, wherein the implant orientation indicator is at the distal end of the handle.

8. The nasal implant delivery tool of claim 1, wherein the implant loading chamber is configured to receive a cartridge containing the nasal implant.

9. The nasal implant delivery tool of claim 8, wherein the cartridge is configured to contain two or more nasal implants.

10. The nasal implant delivery tool of claim 1, wherein the actuator comprises a push-rod, a plunger assembly, and a compression element coupling the push-rod to the plunger assembly.

11. The nasal implant delivery tool of claim 10, wherein the compression element is configured to provide a distal axial force on the nasal implant.

12. The nasal implant delivery tool of claim 10, further comprising a push-rod locking element proximal to the implant loading chamber, wherein the push-rod locking element is configured to limit proximal movement of the push-rod relative to the handle such that the push-rod does not slide entirely out of an interior portion of the handle.

13. The nasal implant delivery tool of claim 12, wherein the push-rod comprises a notch, and wherein the push-rod locking element is configured to engage a notch on the push-rod.

14. The nasal implant delivery tool of claim 10, wherein the needle is movable relative to the handle between a plurality of discrete positions for accommodating nasal implants of different lengths.

15. The nasal implant delivery tool of claim 14, further comprising a needle slider actuator configured to move the needle between the plurality of discrete positions relative to the handle.

16. The nasal implant delivery tool of claim 10, wherein a length of the actuator is adjustable between a first position and a second position, wherein the plunger assembly comprises a first locking surface and a second locking surface, wherein the length of the actuator is at the first position when the push-rod engages the first locking surface of the plunger assembly, and wherein the length of the actuator is at the second position when the push-rod engages the second locking surface on the plunger assembly.

17. The nasal implant delivery tool of claim 1, further comprising an actuator register configured to indicate a position of the actuator corresponding to the nasal implant being at the distal end of the needle, wherein the actuator register comprises a stop element limiting movement of the actuator.

18. The nasal implant delivery tool of claim 1, wherein a portion of the needle lumen that has the non-circular cross-section is configured to control the orientation of the nasal implant.

19. A nasal implant delivery tool comprising:

a handle including an implant loading chamber adapted to receive a nasal implant;

a needle extending distally from the handle to a distal end, wherein the needle comprises a needle lumen having an opening at the distal end, wherein the distal end is sharp;

an actuator configured to move the nasal implant along the needle lumen and toward the opening at the distal end of the needle, wherein the implant loading chamber comprises a non-circular cross-section that is configured to control an orientation of the nasal implant such that the nasal implant is automatically in a predetermined orientation relative to the handle when the nasal implant is at the opening of the needle lumen; and an implant orientation indicator, wherein the implant orientation indicator is configured to provide a visual indication of a plane formed by a first implant arm and a second implant arm of the nasal implant corresponding to the predetermined orientation of the nasal implant in the needle, wherein the implant orientation indicator includes a first indicator arm projecting from the handle in a first direction and a second indicator arm projecting from the handle in a second direction, wherein the first direction is opposite the second direction, and wherein the first indicator arm is directly opposite of the second indicator arm on the handle, wherein the implant loading chamber is configured to receive the nasal implant in the predetermined orientation.

20. The nasal implant delivery tool of claim 19, wherein the first implant arm and the second implant arm have (i) a contracted configuration in which the first implant arm and the second implant arm are contracted toward a central longitudinal axis of the nasal implant and (ii) an expanded configuration in which the first implant arm and the second implant arm extend away from the central longitudinal axis by a greater extent than when the first implant arm and the second implant arm are in the contracted configuration, and wherein the first indicator arm and the second indicator arm define a plane that is substantially parallel to the plane formed by the first implant arm and the second implant arm of the nasal implant when the nasal implant is in the predetermined orientation in the needle.

* * * * *